(12) United States Patent
Bailey et al.

(10) Patent No.: US 11,096,604 B2
(45) Date of Patent: *Aug. 24, 2021

(54) DETERMINING A PRESENCE OF AN OBJECT

(71) Applicant: University of Washington through its Center for Commercialization, Seattle, WA (US)

(72) Inventors: Michael R. Bailey, Seattle, WA (US); Wei Lu, Seattle, WA (US); Oleg A. Sapozhnikov, Seattle, WA (US); Bryan Cunitz, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 253 days.

This patent is subject to a terminal disclaimer.

(21) Appl. No.: 16/178,518

(22) Filed: Nov. 1, 2018

(65) Prior Publication Data

US 2019/0069803 A1 Mar. 7, 2019

Related U.S. Application Data

(63) Continuation of application No. 13/875,973, filed on May 2, 2013, now Pat. No. 10,136,835.

(Continued)

(51) Int. Cl.
*A61B 5/00* (2006.01)
*A61B 5/06* (2006.01)
(Continued)

(52) U.S. Cl.
CPC .............. *A61B 5/06* (2013.01); *A61B 5/201* (2013.01); *A61B 8/085* (2013.01); *A61B 8/0833* (2013.01);
(Continued)

(58) Field of Classification Search
CPC ................................. A61B 5/06; A61B 5/201
See application file for complete search history.

(56) References Cited

U.S. PATENT DOCUMENTS

| 4,324,258 A | 4/1982 | Huebscher et al. |
| 4,907,572 A | 3/1990 | Borodulin et al. |

(Continued)

FOREIGN PATENT DOCUMENTS

WO 2006060492 A2 6/2006

OTHER PUBLICATIONS

Heimdal, Ultrasound Doppler Measurements of Low Velocity Blood Flow: Limitations Due to Clutter Signals from Vibrating Muscles, IEEE Transaction Ultrasonics Ferroelectronics, and Frequency Control, 1997, pp. 873-881, vol. 44.

(Continued)

*Primary Examiner* — Joseph M Santos Rodriguez
(74) *Attorney, Agent, or Firm* — Christensen O'Connor Johnson Kindness PLLC

(57) ABSTRACT

Methods, computing devices, and computer-readable medium are described herein related to producing detection signals configured to induce an excited state of an object. A computing device may receive reflection signals, where the reflection signals correspond to at least one detection signals reflected from the object. Based on the received reflection signals, a presence of the object in the excited state may be determined. Further, an output device may provide an indication of the presence of the object in the excited state.

20 Claims, 15 Drawing Sheets

Related U.S. Application Data

(60) Provisional application No. 61/641,794, filed on May 2, 2012, provisional application No. 61/642,367, filed on May 3, 2012, provisional application No. 61/711,684, filed on Oct. 9, 2012.

(51) Int. Cl.
  *A61B 8/08* (2006.01)
  *A61B 5/20* (2006.01)
  *A61B 8/00* (2006.01)
  *A61B 5/0507* (2021.01)

(52) U.S. Cl.
  CPC ............ *A61B 8/5223* (2013.01); *A61B 8/565* (2013.01); *A61B 5/0507* (2013.01); *A61B 8/488* (2013.01)

(56) References Cited

U.S. PATENT DOCUMENTS

| | | | |
|---|---|---|---|
| 4,962,754 | A | 10/1990 | Okazaki |
| 5,048,527 | A | 9/1991 | Okazaki |
| 5,059,200 | A | 10/1991 | Tulip |
| 5,065,763 | A | 11/1991 | Green et al. |
| 5,240,005 | A | 8/1993 | Viebach |
| 5,425,366 | A | 6/1995 | Reinhardt et al. |
| 5,833,615 | A | 11/1998 | Wu et al. |
| 5,997,477 | A | 12/1999 | Sehgal |
| 6,123,679 | A | 9/2000 | Lafaut et al. |
| 6,186,951 | B1 | 2/2001 | Lizzi et al. |
| 6,206,843 | B1 | 3/2001 | Iger et al. |
| 6,221,018 | B1 | 4/2001 | Ramamurthy et al. |
| 6,385,474 | B1 | 5/2002 | Rather et al. |
| 6,425,869 | B1 | 7/2002 | Rafter et al. |
| 6,716,184 | B2 | 4/2004 | Vaezy et al. |
| 6,728,567 | B2 | 4/2004 | Rather et al. |
| 7,273,458 | B2 | 9/2007 | Prausnitz et al. |
| 7,456,019 | B2 | 11/2008 | Goodwin et al. |
| 7,485,101 | B1 | 2/2009 | Faragalla |
| 8,038,616 | B2 | 10/2011 | Angelsen et al. |
| 8,057,408 | B2 | 11/2011 | Cain et al. |
| 2002/0045821 | A1 | 4/2002 | Tsuzuki |
| 2002/0065466 | A1 | 5/2002 | Rather et al. |
| 2003/0028111 | A1 | 2/2003 | Vaezy et al. |
| 2003/0163048 | A1 | 8/2003 | Rafter et al. |
| 2003/0204141 | A1 | 10/2003 | Nock et al. |
| 2004/0006288 | A1 | 1/2004 | Spector et al. |
| 2004/0024315 | A1 | 2/2004 | Chalana et al. |
| 2004/0059265 | A1 | 3/2004 | Candy et al. |
| 2004/0059319 | A1 | 3/2004 | Bohris |
| 2004/0111016 | A1 | 6/2004 | Casscells, III et al. |
| 2006/0052699 | A1 | 3/2006 | Angelsen et al. |
| 2006/0240550 | A1 | 10/2006 | Goodwin et al. |
| 2008/0091125 | A1 | 4/2008 | Owen et al. |
| 2008/0146908 | A1 | 6/2008 | Wu |
| 2008/0319356 | A1 | 12/2008 | Cain et al. |
| 2009/0177085 | A1 | 7/2009 | Maxwell et al. |
| 2009/0227992 | A1 | 9/2009 | Nir et al. |
| 2009/0230822 | A1 | 9/2009 | Kushculey et al. |
| 2009/0264754 | A1 | 10/2009 | Dahl et al. |
| 2009/0275866 | A1 | 11/2009 | Gelbart et al. |
| 2009/0299187 | A1 | 12/2009 | Bailey et al. |
| 2010/0036255 | A1 | 2/2010 | Itani |
| 2010/0056924 | A1 | 3/2010 | Powers |
| 2010/0256534 | A1 | 10/2010 | Lacoste et al. |
| 2011/0251528 | A1 | 10/2011 | Canney et al. |
| 2011/0263967 | A1 | 10/2011 | Bailey et al. |
| 2013/0072854 | A1 | 3/2013 | Mohan et al. |
| 2013/0303906 | A1 | 11/2013 | Cain et al. |

OTHER PUBLICATIONS

Jensen, Stationary Echo Canceling in Velocity Estimation by Time-Domain Cross-Correlation, IEEE Transactions on Medical Imaging, No. 3, 1993, pp. 471-477, vol. 12.

Kim, et al., Color Doppler Twinkling Artifacts in Various Conditions During Abdominal and Pelvic Sonography, J Ultrasound Med., 2010, 621-632, American Institute of Ultrasound in Medicine.

Chelfouh, et al., Characterization of Urinary Calculi: In Vitro Study of Twinkling Artifact Revealed by Color-Flow Sonography, AJR, Oct. 1998, 1055-1060, ARRS, 171.

Shabana, et al. (2009) "Comparison between color Doppler twinkling artifact and acoustic shadowing for renal calculus detection: an in vitro study," Ultrasound in Medicine and Biology, 35(2): 339-350.

Rosenschein, et al. (2000) "Ultrasound imaging-guided noninvasive ultrasound thrombolysis: preclinical results," Circulation, 10 2(2): 238-245.

Albala, et al.: Lower Pole 1: A Prospective Randomized Trial of Extracorporeal Shock Wave Lithotripsy and Nephrostolithotomy for Lower Pole Nephrolithiasis—Initial Results. The Journal of Urology, 166: 2072, 2001.

Pearle, et al: Prospective Randomized Trial Comparing Shock Wave Lithotripsy and Ureteroscopy for Lower Pole Caliceal Calculi 1 em or Less. The Journal of Urology, 179: S69, 2008.

Chen, et al.: Extracorporeal Shock Wave Lithotripsy for Lower Pole Calculi: Long-term Radiographic and Clinical Outcome. The Journal of Urology, 156: 1572, 1996.

Sampaia, et al.: Limitations of extracorporeal shockwave lithotripsy for lower caliceal stones: anatomic insight. J Endourol, 8:241, 1994.

Chiong, et al.: Randomized controlled study of mechanical percussion, diuresis, and inversion therapy to assist passage of lower pole renal calculi after shock wave lithotripsy. Urology, 65: 1070, 2005.

Kekre, et al.: Optimizing the fragmentation and clearance after shock wave lithotripsy. Curr Opin Ural, 18: 205, 2008.

Pace, et al.: Mechanical percussion, inversion and diuresis for residual lower pole fragments after shock wave lithotripsy: a prospective, single blind, randomized controlled trial. J Ural, 166: 2065, 2001.

International Search Report for PCT/US2011/033652, dated Dec. 12, 2011.

Krings. et al.. "Extracorporeal Shock Wave Lithotripsy Retreatment ("Stir-Up") Promotes Discharge of Persistent Caliceal Stone Fragments After Primary Extracorporeal Shock Wave Lithotripsy", The Journal of Urology, 1992, vol. 148, 1040-1042.

Parr, et al., "Does Further Extracorporeal Lithotripsy Promote Clearance of Small Residual Fragments?", British Journal of Urology, 1991, 68, 565-567.

Shah, et al., "Novel ultrasound method to reposition kidney stones", Ural Res, 2010, 38:491-495.

Khan, et al., "Twinkling Artifact on Intracerebral Color Doppler Sonography", AJNR Am J_ Neuroradiol 20: Feb. 1999, pp. 246-247.

Riccabona, Michael, "Potential of Modern Sonographic Techniques in Paediatric Uroradiology", European Journal of Radiology 43, 2002, pp. 110-121.

O'Brien, Jr. et al, The Risk of Exposure to Diagnostic Ultrasound in Postnatal Subjects Thermal Effects, J Ultrasound Med, 2008, 517-535, 27.

Non-Final Office Action, dated Apr. 12, 2016, in U.S. Appl. No. 14/278,197, filed May 15, 2014, 25 pages.

Final Office Action, dated Oct. 6, 2016, in U.S. Appl. No. 14/278,197, filed May 15, 2014, 25 pages.

Andrulli, et al. Colour Doppler twinkling in kidney stones: artefact of sign?, NDT Plus (2010) 3:151-154.

Dillman, et al. Sonographic twinkling artifact for renal calculus detection: correlation with CT, Radiology: vol. 259:No. 3—Jun. 2011.

DETERMINING A PRESENCE OF AN OBJECT

CROSS-REFERENCE TO RELATED APPLICATIONS

This application claims priority to: (1) U.S. Provisional Patent App. No. 61/641,794, entitled "Using Bubbles to Better Detect Kidney Stones," filed on May 2, 2012, (2) U.S. Provisional Patent App. No. 61/642,367, entitled "Using Bubbles to Better Detect Kidney Stones," filed on May 3, 2012, and (3) U.S. Provisional Patent App. No. 61/711,684, entitled "Method and Device to use Ultrasound to Facilitate Kidney Stone Passage," filed on Oct. 9, 2012, the contents of which are fully incorporated by reference herein for all purposes.

STATEMENT OF U.S. GOVERNMENT INTEREST

This invention was made with government support under DK43881 and 1R01DK092197, each awarded by the National Institutes of Health. The government has certain rights in the invention.

BACKGROUND

Unless otherwise indicated herein, the materials described in this section are not prior art to the claims in this application and are not admitted to be prior art by inclusion in this section.

Non-invasive procedures may involve making observations underneath the skin of a mammal without breaking the skin of the mammal. Various non-invasive procedures today face challenges with the detection of an object underneath the skin. For example, an object may include a foreign object such as a catheter or a stent. In other instances, an object may include a gall stone, a salivary duct stone, various tissues, a blood vessel, plaque, and/or a bone fragment, among other examples.

In one particular area of study, minerals and salts in kidneys may cluster and form crystals in urine, accumulating into kidney stones. Small kidney stones may be able to pass out of the body with urine, possibly unnoticed. However, larger kidney stones may block, stretch, and/or irritate a tube called the ureter that connects the kidney to the bladder. Passing larger kidney stones through the ureter may cause excruciating pain. Notable symptoms have been described as radiating pain starting in the lower back and then continuing on to the groin and genitals as the kidney stone passes with urine out of the body.

The prevalence of kidney stone disease is increasing in humans. Considerable studies have shown a moderate growth in the percentage of the population affected by the disease. Further, additional studies have indicated that approximately half of newly diagnosed patients will have a recurrent stone within five to ten years of detecting a first kidney stone. In particular, recurrent stones may develop due to residual crystals continuously growing over time.

SUMMARY

Various embodiments set forth herein provide ways of detecting objects in tissue based on signals. These embodiments are provided herein for purposes of illustration and are not meant to be limiting in any way.

In one aspect, a computer-implemented method may include producing one or more detection signals configured to induce an excited state of an object. Further, the method may include receiving one or more reflection signals, where the one or more reflection signals correspond to at least one of the one or more detection signals reflected from the object. Yet further, based on the received one or more reflection signals, the method may include determining a presence of the object in the excited state. In addition, the method may include causing an output device to provide an indication of the presence of the object in the excited state.

In another aspect, a computing device may include a processor and a non-transitory computer-readable medium configured to store program instructions that, when executed by the processor, cause the computing device to carry out functions. The functions may include producing one or more detection signals configured to induce an excited state of an object. Further, the functions may include receiving one or more reflection signals, where the one or more reflection signals correspond to at least one of the one or more detection signals reflected from the object. Yet further, based on the received one or more reflection signals, the functions may include determining a presence of the object in the excited state. In addition, the functions may include causing an output device to provide an indication of the presence of the object in the excited state.

A non-transitory computer-readable medium including program instructions that, when executed by a processor, cause the processor to perform functions including producing one or more detection signals configured to induce an excited state of an object. Further, the functions may include receiving one or more reflection signals, where the one or more reflection signals correspond to at least one of the one or more detection signals reflected from the object. Yet further, based on the received one or more reflection signals, the functions may include determining a presence of the object in the excited state. In addition, the functions may include causing an output device to provide an indication of the presence of the object in the excited state.

In yet a further aspect, a system may include: (a) a means for producing one or more detection signals configured to induce an excited state of an object (b) a means for receiving one or more reflection signals, where the one or more reflection signals correspond to at least one of the one or more detection signals reflected from the object, (c) based on the received one or more reflection signals, a means for determining a presence of the object in the excited state, (d) a means for causing an output device to provide an indication of the presence of the object in the excited state.

These as well as other aspects, advantages, and alternatives will become apparent to those of ordinary skill in the art by reading the following detailed description, with reference where appropriate to the accompanying drawings. Further, it should be understood that this summary and other descriptions and Figures provided herein are intended to illustrative embodiments by way of example only and, as such, that numerous variations are possible. For instance, structural elements and process steps can be rearranged, combined, distributed, eliminated, or otherwise changed, while remaining within the scope of the embodiments as claimed.

DETAILED DESCRIPTION

Figure 1:
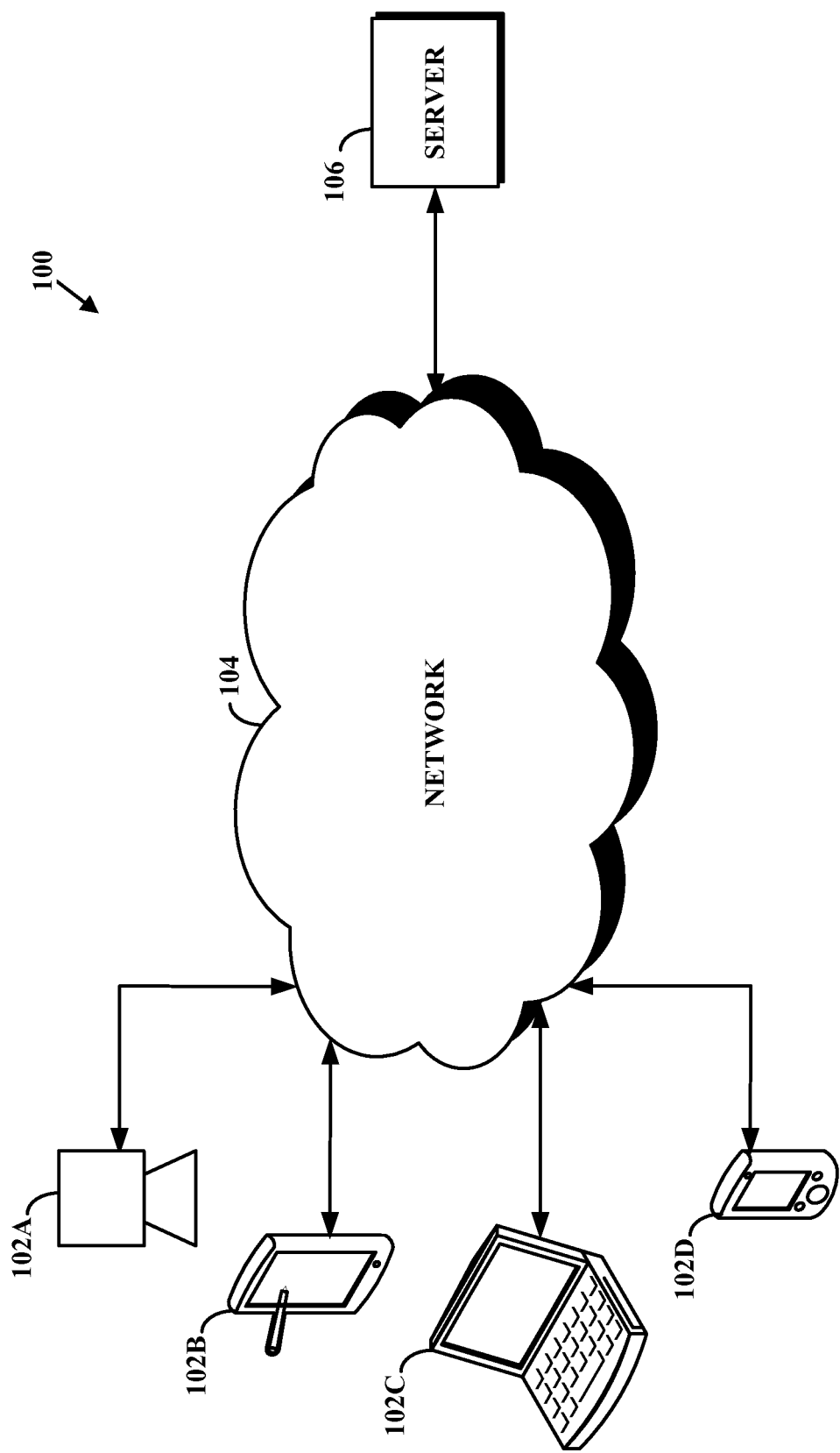
FIG. 1 shows a simplified block diagram of an example communication network in which at least one embodiment can be implemented.

In the following detailed description, reference is made to the accompanying Figures, which form a part thereof. In the Figures, similar symbols typically identify similar components, unless context dictates otherwise. The illustrative embodiments described in the detailed description, Figures, and claims are not meant to be limiting. Other embodiments may be utilized, and other changes may be made, without departing from the spirit or scope of the subject matter presented herein. It will be readily understood that aspects of the present disclosure, as generally described herein, and illustrated in the Figures, can be arranged, substituted, combined, separated, and/or designed in a wide variety of different configurations, all of which are explicitly contemplated herein.

1. OVERVIEW

In an example embodiment, a computing device may produce detection signals that may be used to detect an object. In some instances, the computing device may produce detection signals from a probe coupled to the computing device. The detection signals may penetrate through a medium and reflect off an object in the medium. Some of the reflected signals may return to the computing device and/or the probe, or possibly another device coupled to the computing device. The reflected signals may be used to detect the presence of the object. For example, a computing device positioned outside of a mammal may produce detection signals that penetrate through the mammal's skin, reflect off a kidney stone in the mammal's kidney, and return to the computing device. As such, the reflection signals returned to the probe may provide information indicating the presence of the kidney stone in the mammal's kidney.

In an additional embodiment, the computing device may produce detection signals that excite the object. For example, the computing device may produce detection signals, such as excitation pulses, that interact with and/or excite the object. In some instances, excitation pulses may be amplified signals may interact with the object. Further, amplified signals may interact with reflection items on the object, such as bubbles inside and/or on the surface of the object. In particular, the amplified signals may cause the bubbles to get bigger and change shape. The excited object may be referred to as a twinkling artifact.

Further, in an additional embodiment, the computing device may receive reflection signals from an excited object. Such reflection signals may be used to detect the excited object. In particular, such reflection signals may have different characteristics than signals reflected from objects that are not excited. By observing such differences, excited objects may be detected. As such, in some examples, detection signals may be configured to induce the excited state of an object and the reflection signals may detect the excited object.

In some instances, characteristics of the detection signals such as amplitude may be configured to induce an excited state of the object. Further, it should be noted that various terms referring to respective objects such as a kidney stone, a twinkling artifact, an excited object, and an object induced to an excited state may be used interchangeably, as described herein. Further, exciting the object, interacting with a bubble on the object, exciting a bubble on the object, oscillating the bubble on the object, and/or other similar expressions may also be used interchangeably.

In addition, it should also be noted that the examples of bubbles on an object in the above description are provided for illustrative purposes and should not be construed as limiting. Inducing an excited state of an object may depend on other reflection items as well. For example, cavitation of the object may include impurities where bubbles appear and grow. Further, reflection items may include calcification, crevices, cracks, and/or concretions associated with the object.

In some instances, an object may be naturally created in the medium. For example, an object may be a kidney stone originated from the accumulation of substances such as minerals and salts in a mammal's kidneys. Yet further, objects may be formed from the clustering of crystals in the mammal's urine. However, it should be noted that objects may also be foreign and/or artificial objects found in the mammal's body. Other possibilities may also exist.

In some embodiments, an indication of the excited object may be provided on an output device (e.g., a graphical display) and the output device may provide further information regarding the excited object. In particular, harmonic imaging of the object may provide information regarding the location of a kidney stone within the kidney, any movements of the kidney stone within the kidney, characteristics of the kidney stone (e.g., size, shape, and/or composition), among other possibilities.

2. EXAMPLE ARCHITECTURE

FIG. 1 shows a simplified block diagram of an example communication network in which at least one embodiment can be implemented. It should be understood that this and other arrangements described herein are set forth only as examples. Those skilled in the art will appreciate that other arrangements and elements (e.g., medical devices, laboratory machines, interfaces, functions, orders, and groupings of functions, etc.) can be used instead and that some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. And various functions described herein may be carried out by a processor executing instructions stored in memory.

As shown in FIG. 1, example network 100 includes various network-access devices 102A-102D, network 104 such as the Internet, and server 106. As illustrated, network-access devices 102A, 102B, 102C, and 102D may be a computing device (e.g., a portable medical device), a tablet computer, a laptop computer and/or a desktop personal computer (PC), and a mobile phone, respectively. It should be noted that network-access device 102A may be described as a computing device for carrying out process, methods, and functions further described herein. As such, network-access devices 102B-102D, network 104, and server 106 may be described for purposes of illustrating that various processes, steps, and/or functions may be distributed and performed by other devices, networks, and/or servers. For example, network-access devices 102B-102D may be stand-alone devices or may be coupled to network-access device 102A for carrying out various processes. Thus, it should be noted that additional entities and devices not depicted in FIG. 1 could be present as well.

Network 104 may be a public network or a private network (e.g., a local network in a laboratory, a clinic, and/or a doctor's office). As an example, there could be more network-access devices and more servers in communication with network 104. Other network elements may be in communication with network 104 as well. Also, there could be one or more devices and/or networks making up at least part of one or more of the communication links depicted in FIG. 1. As an example, there could be one or more routers, switches, or other devices or networks on the communication links between network-access devices 102A-102D, network 104, and/or server 106. Each of network-access devices 102A-102D may be any network-access device arranged to carry out the network-access device functions described herein.

Systems and devices in which example embodiments can be implemented will now be described in greater detail. In general, an example system may be implemented in and/or can take the form of a computing device. In an example embodiment, network-access device 102A may be described as a computing device including an engine capable of producing detection signals and receiving reflection signals. Further, the computing device may be portable, hand-held, and/or transferable by a single person.

Figure 2:
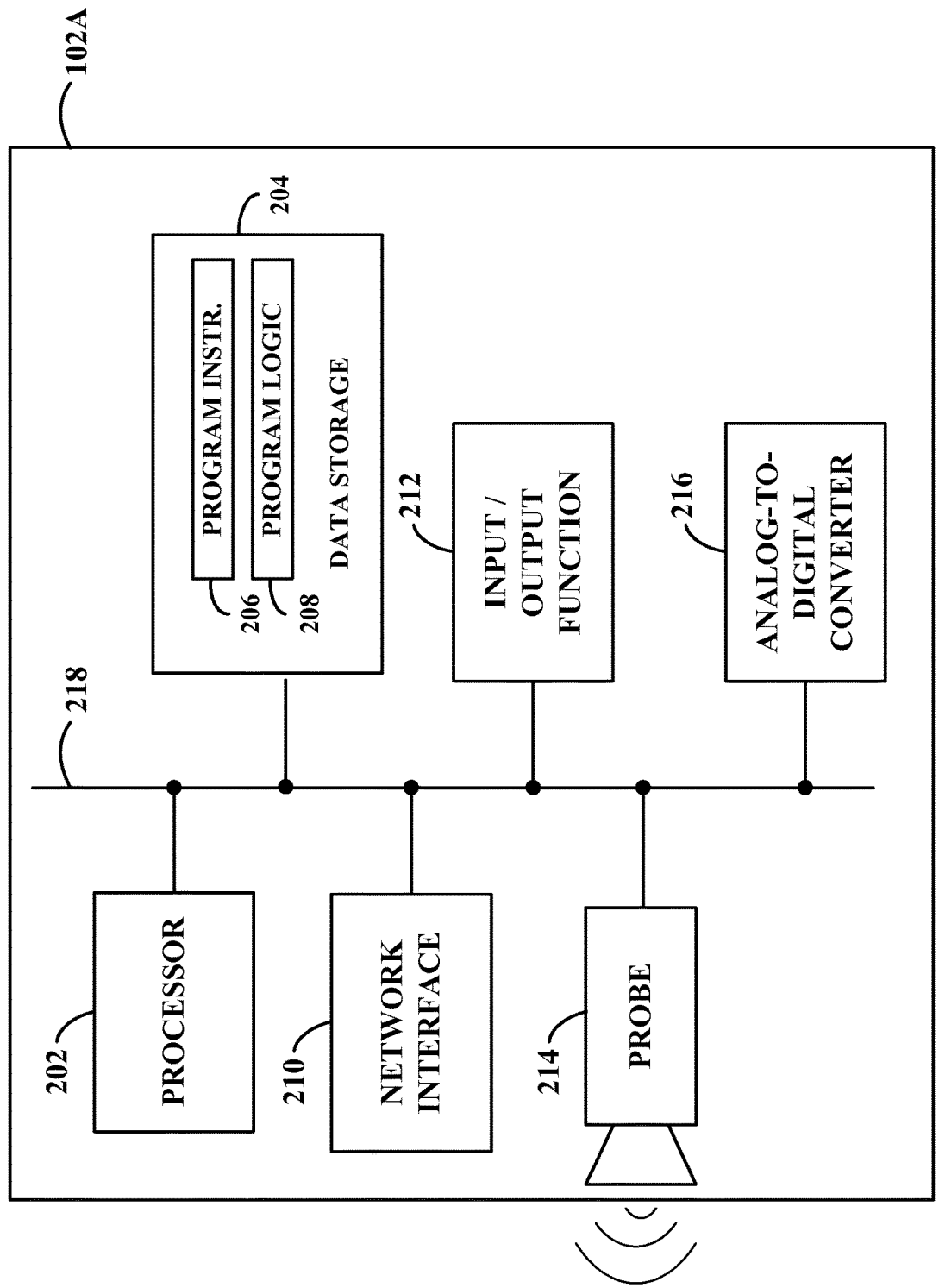
FIG. 2 shows a simplified block diagram of a network-access device arranged to implement aspects of at least one embodiment.

FIG. 2 shows a simplified block diagram of a computing device arranged to implement aspects of at least one embodiment. For example, network-access device 102A may include processor 202, data storage 204, and network interface 210, all linked together via system bus, network, or other connection mechanism 218.

Processor 202 may include one or more general purpose microprocessors, central processing units (CPUs), and/or dedicated signal processors. In addition, processor 202 may include one or more application specific integrated circuits (ASICs), digital signal processors (DSPs), and may be integrated in whole or in part with network interface 210. Data storage 204 may include memory and/or other storage components, such as optical, magnetic, organic or other memory disc storage, which can be volatile and/or non-volatile, internal and/or external, and integrated in whole or in part with processor 202. Data storage 204 may be arranged to contain (i) program instructions 206 and (ii) program logic 208, executable by processor 202. Data storage 204 may also store data that may be manipulated by processor 202 to carry out the various methods, processes, or functions described herein.

In some embodiments, these methods, processes, or functions can be defined by hardware, firmware, and/or any combination of hardware, firmware and software. Therefore, data storage 204 may include a tangible, non-transitory computer-readable medium, having stored thereon program instructions that, upon execution by one or more processors, cause computing device 102A to carry out any of the methods, processes, or functions disclosed in this specification or the accompanying drawings.

Although these components are described herein as separate data storage elements, the elements could just as well be physically integrated together or distributed in various other ways. For example, program instructions 206 may be maintained in data storage 204 separate from program logic 208, for easy updating and reference by program logic 208.

Network interface 210 may enable network-access device 102A to send communication and receive communication. Network interface 210 typically functions to communicatively couple network-access device 102A to networks, such as network 104. As such, network interface 210 may include a wired (e.g., Ethernet) and/or wireless (e.g., Wi-Fi, BLUETOOTH®, or a wide-area wireless connection) packet-data interface, for communicating with other devices, entities, and/or networks.

Input/output function 212 may facilitate user interaction with an example computing device 100. Input/output function 212 may comprise multiple types of input devices, such as a keyboard, a mouse, a touch screen, a probe, a transducer, a sensor, and/or any other device that is capable of receiving input. Similarly, input/output function 212 may comprise multiple types of output devices, such as a graphical display, a printer, one or more light emitting diodes (LEDs), speaker configured to generate audible sounds, or any other device that is capable of providing output discernible to a user. Additionally or alternatively, example computing device 102E may support remote access from another device, via network interface 210 or via another interface (not shown), such an RS-132 or Universal Serial Bus (USB) port.

Probe 214 may produce one or more radio frequency pulses, radio frequency pulses produced within a first time period (e.g., 333 microseconds), a sequence of substantially similar radio frequency pulses produced within a time period different than the first time period, a sound wave, a sound pressure wave, and/or an oscillating sound pressure wave. In the examples above, the first time period may be 200-400 microseconds, among other possible ranges. In particular, probe 214 may produce such pulses in response to executing program instructions 206 stored in data storage 204 and communicating to probe 214 via other connection mechanism 218. Probe 214 may also produce signals within one or more time periods. Yet further, in some instances, any one of the signals may be produced within a given time period and other detection signals may be produced within a different time period. In some instances, probe 214 may produce, ultrasound propagation or arrays, Doppler signals, among other possibilities. In particular, probe 214 may produce one or more pulses that contain a series of 10-30 identical pulses or bursts, 1-10 cycles of such bursts, and where the pulses are transmitted with a central frequency of 2 to 8 MHz. In some instances, the pulses may have a 1-5 kHz pulse-repetition frequency (PRF). It should be noted that a probe, such as probe 214, may be similar to a transducer such that a probe and a transducer may be used interchangeably herein.

In some instances, probe 214 may produce detection signals such as excitation pulses. Further, in some instances, detection signals may have 2 to 5 cycles. Yet further, in some instances, positive pressures (P+) and negative pressures (P−) of pressure detections signals may be 1 to 5 MPa and −5 to −1 MPa, respectively. Probe 214 may also receive signals reflected from external objects back to probe 214. Computing device 100 may also receive signals through a sensor or another device, possibly connected through input/output function 212. As noted, detection signals may be configured to induce an excited state of an object. As such, it should be understood that the above-characteristics of detection signals may be configured to induce the excited state of an object.

It should be noted that probe 214 may be removable so as to operate while being physically separate from computing device 100. For example, probe 214 may communicate remotely with computing device 110 through input/output function 212. In some instances, there may be several probes similar to probe 214 that may move remotely, controlled by computing device 110.

Reflected signals received by probe 214 may be converted to digital signals through analog-to-digital converter (ADC) 216. ADC 216 may be a 12-24 bit analog-to-digital converter configured to sample signals at a 10-30 MHz frequency. For example, signals transmitted by probe 214 may be received by probe 214 and converted to digital signals through ADC 216. In some instances, digitized signals from ADC 216 may also be processed in real-time using mathematical software platforms. In some instances, unmodified signal outputs from ADC 216 may identify characteristics of objects for detecting the objects. It should be noted that computing device 102A may also include one or more digital-to-analog converters (not illustrated) that may be configured to transmit signals to probe 214. As such, probe 214 may produce detection signals as described herein.

In some instances, computing device 102A may modify the reflected signals received by probe 214. In some instances, signals may be modified by band-pass filters, analog filters, amplifiers, and clipping diodes (not shown in FIG. 2). In particular, signals may be modified by an anti-aliasing band-pass filter with a 0.7 to 17 MHz bandwidth. Further, signals may be amplified using time-gain compensation. Yet further, signals may be limited and/or clipped by a diode. In some instances, the modification described herein may be implemented through signal processing software. It should be noted that the above-referenced modifications to the reflected signals may occur before being sampled by ADC 216.

Figure 3:
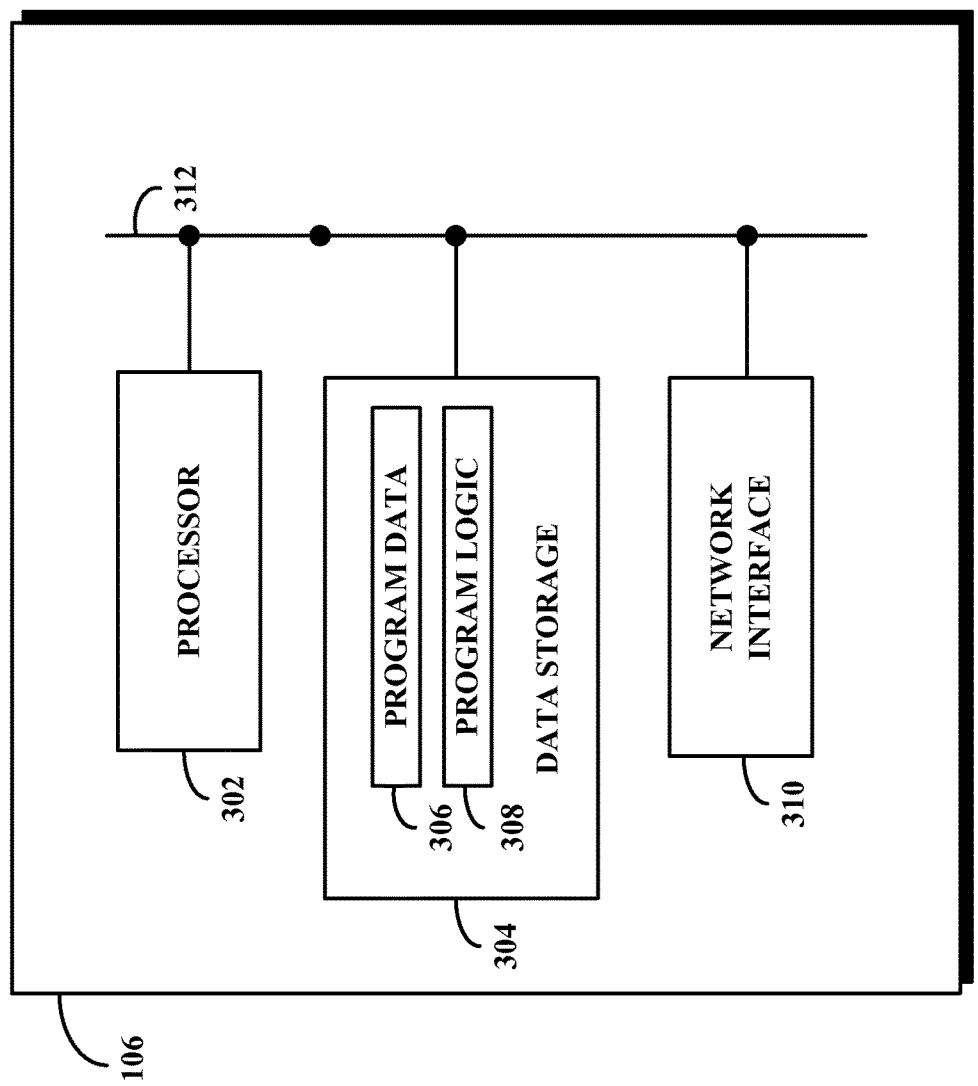
FIG. 3 shows a simplified block diagram of a server arranged to implement aspects of at least one embodiment.

Server 106 may be any network server or other computing system arranged to carry out the server functions described herein including, but not limited to, those functions described with respect to FIGS. 5-10. In particular, reflection signal received by probe 214 may be communicated to server 106 for analysis, possibly to detect an excited object. As such, network-access device 102A and server 106 may share processes, methods, and/or functions described herein for determining the presence of the excited object. FIG. 3 shows a simplified block diagram of a server arranged to implement aspects of at least one embodiment. As such, shown in FIG. 3, server 106 may include processor 302, data storage 304 including program data 306 and program logic 308, and network interface 310, all linked together via system bus, network, and/or other connection mechanism 312. Processor 302, data storage 304, program data 306, program logic 308, and network interface 310 may be configured and/or arranged similar to processor 202, data storage 204, program instructions 206, program logic 208, and network interface 210, respectively, as described above with respect to network-access device 102A.

Data storage 304 may contain information used by server 106 in operation. For example, date storage 304 may include instructions executable by the processor for carrying out the server functions described herein including, but not limited to, those functions described below with respect to FIGS. 5-10. As another example, data storage 304 may contain various design logic and/or design data used for determining a test result, such as the logic and data described below with respect to FIGS. 5-10. Generally, data storage 304 may contain information used by server 106 to provide information accessible by various network-access devices, such as network-access device 102A, over network 104.

Returning to FIG. 1, network 104 may also include one or more wide area networks, one or more local area networks, one or more public networks such as the Internet, one or more private networks, wired networks, wireless networks, and/or networks of any other variety. Devices in communication with network 104 (including, but not limited to, network-access devices 102A-102D and server 106) may exchange data using a packet-switched protocol such as IP, and may be identified by an address such as an IP address.

Figure 4:
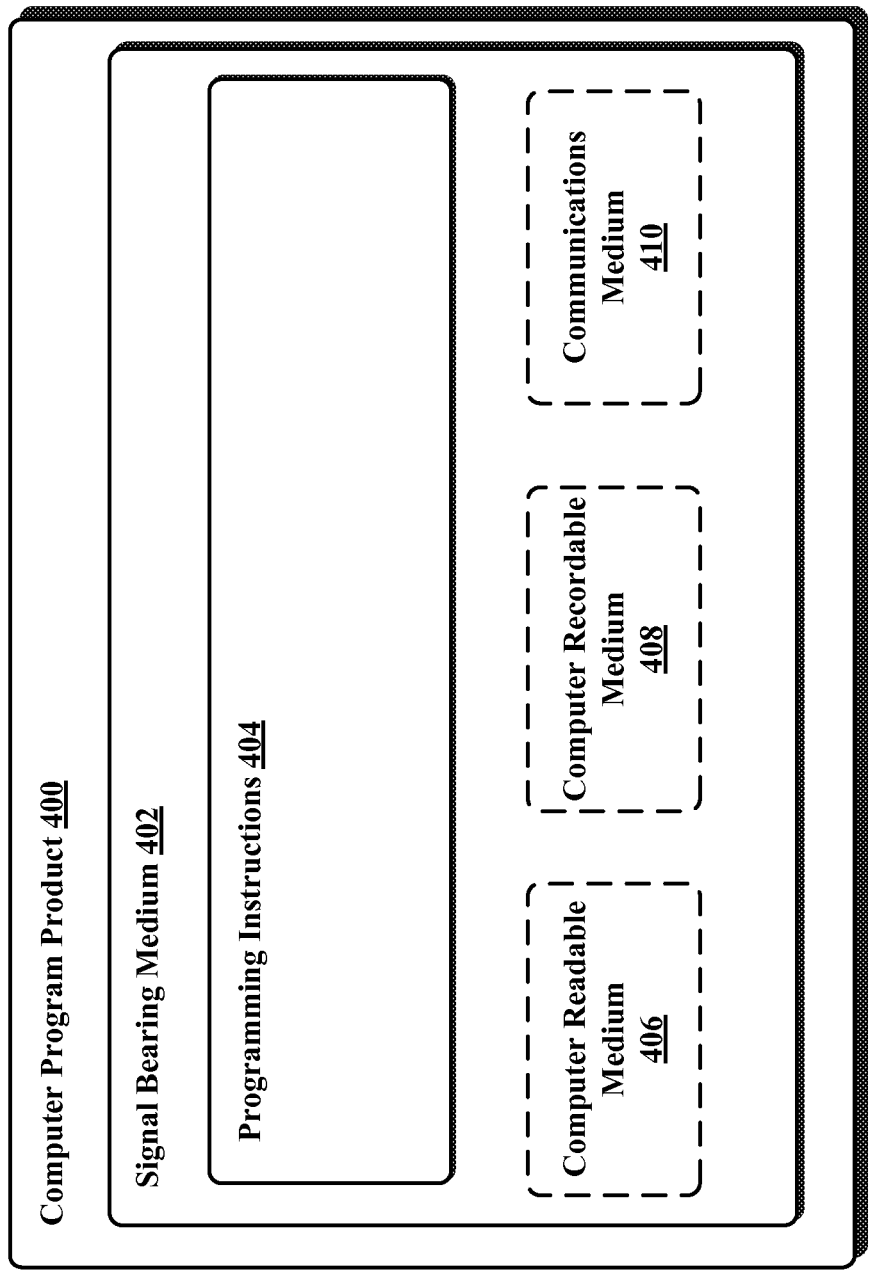
FIG. 4 depicts an example computer-readable medium arranged to implement aspects of at least one embodiment.

As noted above, in some embodiments, the disclosed methods may be implemented by computer program instructions encoded on a physical and/or non-transitory computer-readable storage media in a machine-readable format, or on other non-transitory media or articles of manufacture. FIG. 4 is a schematic illustrating a conceptual partial view of an example computer program product that includes a computer program for executing a computer process on a network-access device, arranged according to at least some embodiments presented herein.

In one embodiment, the example computer program product 400 is provided using a signal bearing medium 402. The signal bearing medium 402 may include one or more programming instructions 404 that, when executed by one or more processors may provide functionality or portions of the functionality described herein. In some examples, the signal bearing medium 402 may encompass a computer-readable medium 406, such as, but not limited to, a hard disk drive, a Compact Disc (CD), a Digital Video Disk (DVD), a digital tape, memory, etc. In some implementations, the signal bearing medium 402 may encompass a computer recordable medium 408, such as, but not limited to, memory, read/write (R/W) CDs, R/W DVDs, etc.

In some implementations, the signal bearing medium 402 may encompass a communications medium 410, such as, but not limited to, a digital and/or an analog communication medium (e.g., a fiber optic cable, a waveguide, a wired communications link, a wireless communication link, etc.). Thus, for example, the signal bearing medium 402 may be conveyed by a wireless form of the communications medium 410. It should be understood, however, that computer-readable medium 406, computer recordable medium 408, and communications medium 410 as contemplated herein are distinct mediums and that, in any event, computer-readable medium 408 is a physical, non-transitory, computer-readable medium.

The one or more programming instructions 404 may be, for example, computer executable and/or logic implemented instructions. In some examples, a computing device such as the network-access device 102A of FIG. 2 may be configured to provide various operations, functions, or actions in response to the programming instructions 404 conveyed to the network-access device 102A by one or more of the computer readable medium 406, the computer recordable medium 408, and/or the communications medium 410.

The physical and/or non-transitory computer readable medium could also be distributed among multiple data storage elements, which could be remotely located from each other. The computing device that executes some or all of the stored instructions could be a network-access device such as the network-access device 102A illustrated in FIG. 2. Alternatively, the computing device that executes some or all of the stored instructions could be another computing device, such as a server, for instance server 106 illustrated in FIG. 3.

3. EXAMPLE METHOD FOR DETECTING AN OBJECT

Figure 5:
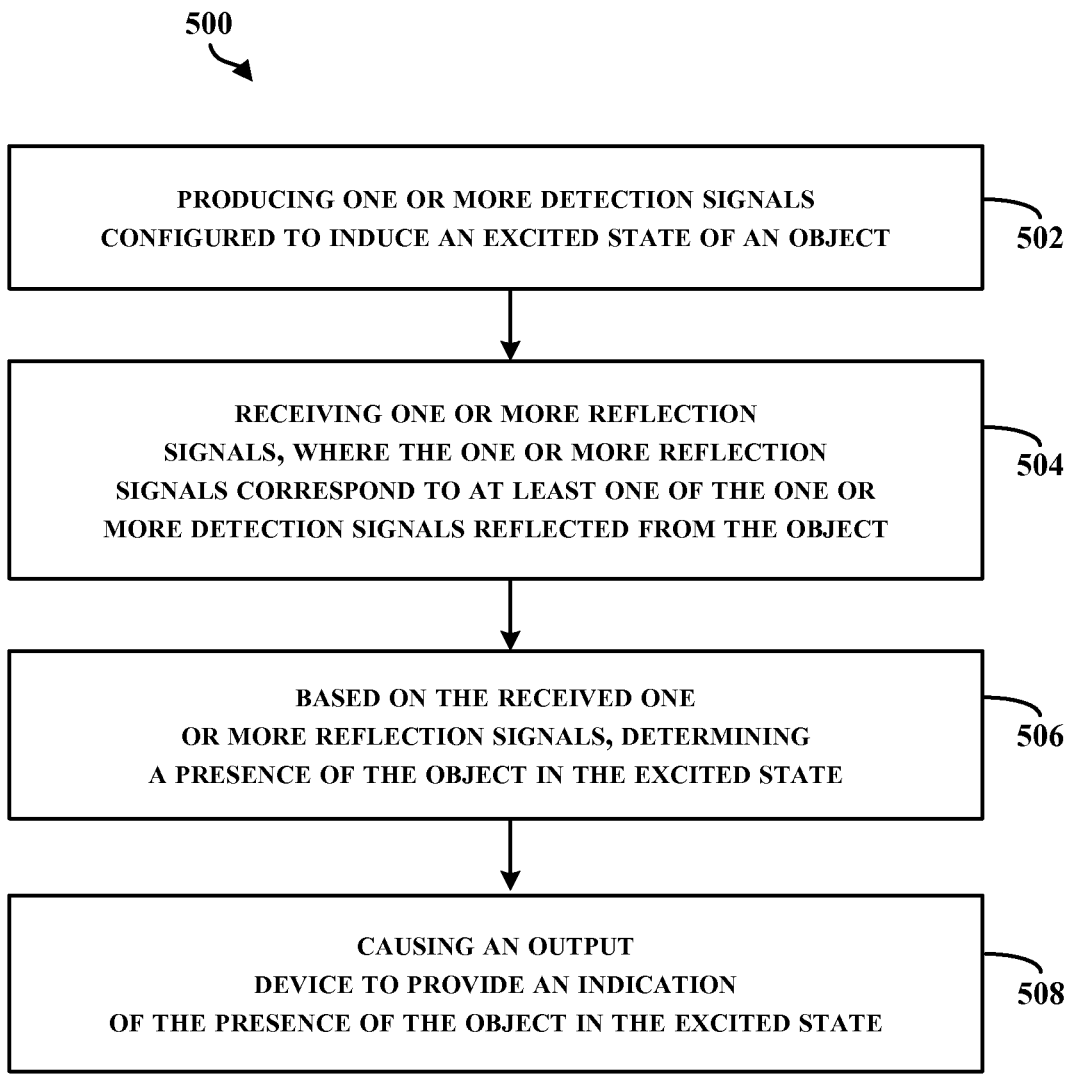
FIG. 5 is a simplified flow chart depicting aspects of an example method.

FIG. 5 shows a simplified flow chart depicting aspects of an example method for detecting an object as described herein. For purposes of example and explanation, aspects of such example methods are described with reference to an example computing device. It should be understood, however, that the example methods described herein may apply just as well to any suitable computing device including, but not limited to, a computing device integrated with a computer, a mobile computing device, a medical device, and/or other computing system, among other examples.

Figure 6A:
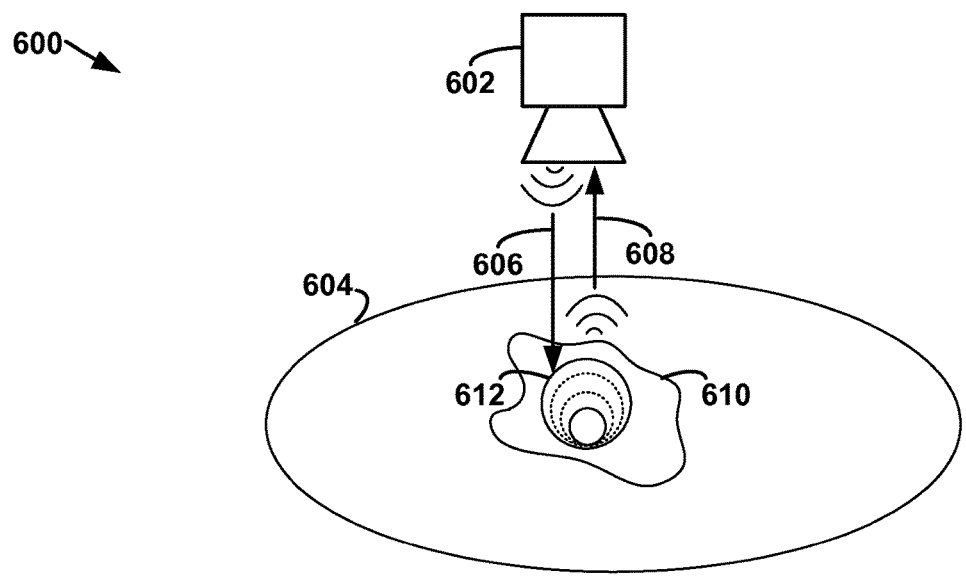
FIG. 6A depicts aspects of a computing device in accordance with one or more example embodiments.
Figure 6B:
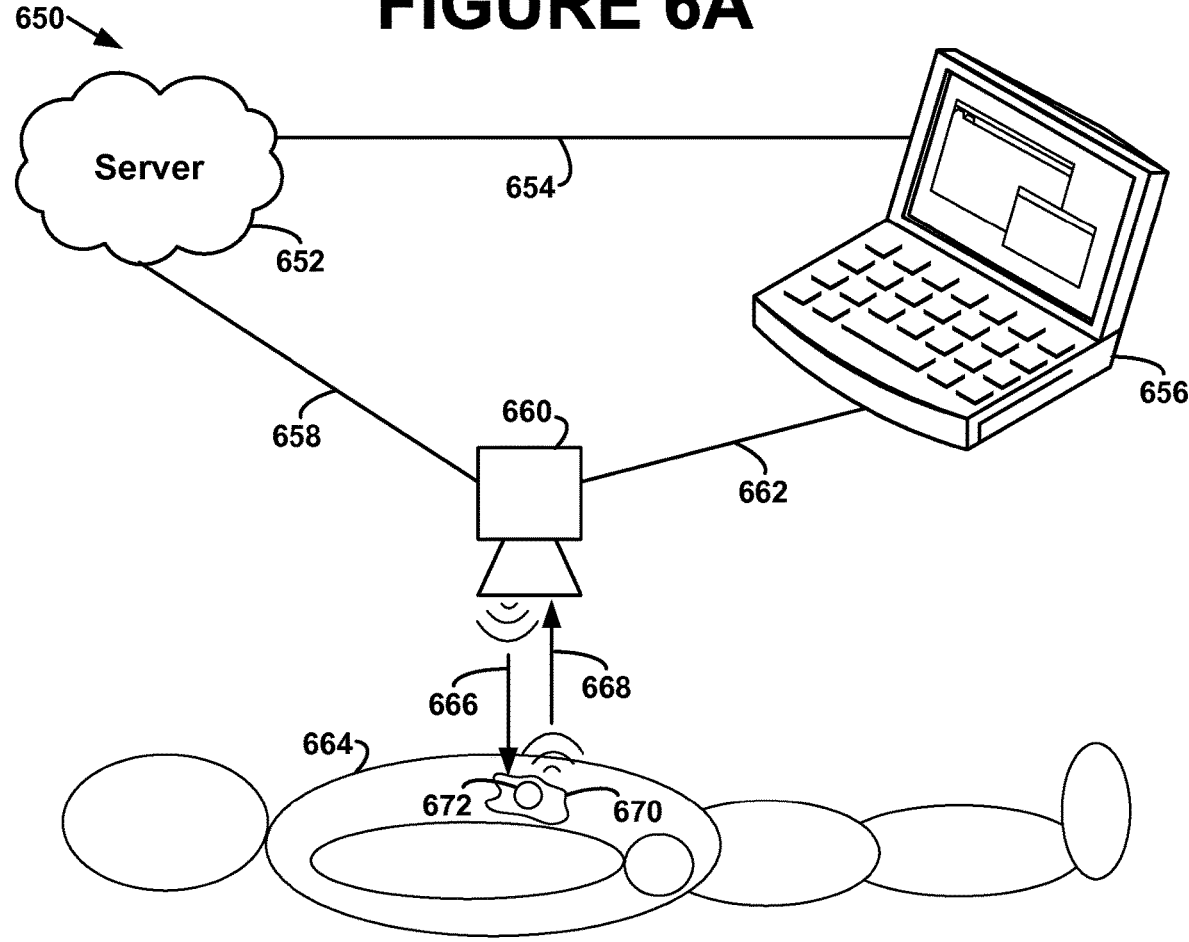
FIG. 6B depicts aspects of another computing device in accordance with one or more example embodiments.

FIGS. 6A and 6B depict aspects of example computing devices in accordance with one or more example embodiments. More particularly, FIGS. 6A and 6B depict aspects of a computing device illustrated in FIG. 5 for carrying out the method for detecting an object. For example, computing device 602 depicts aspects of an example computing device detecting an object. Various respective features, characteristics, and/or functionality of the computing devices depicted in FIGS. 6A and 6B are discussed further below with respect to the example methods described herein.

In FIG. 5, method 500 is described by way of example as being carried out by a computing device, possibly a computing device coupled to a probe. For example, method 500 may be carried by network-access device 102 and/or computing device 602. Further, example methods, such as method 500, can be carried out by devices other than a computing device and/or can be carried out by sub-systems in a computing device. For example, method 500 may also be carried out by network-access devices 102B-102D, network 104, and/or server 106. In some instances, an example method can be carried out by a computing device which is programmed to display an excited object on a graphical display.

As shown in FIG. 5, method 500 begins at block 502 with a computing device, such a computing device coupled to a probe, which may carry out functions for producing one or more detection signals configured to induce an excited state of an object. At block 504, the computing device receives one or more reflection signals, where the reflection signals correspond to at least one of the detection signals reflected from the object. At block 506, based on the received one or more reflection signals, the computing device determines a presence of the object in the excited state. At block 508, the computing device causes an output device to provide an indication of the presence of the object in the excited state.

The steps of method 500 are explained in the following subsections. Although method 500 may be carried out by network-access device 102A, this is not required. Various steps illustrated by these flow charts may be carried out by other types of devices or systems, such as server 106. Further, it may be possible to distribute aspects of individual steps between network-access devices 102A-102B, network 104, and server 106. For instance, network-access device 102A may produce detection signals and receive reflection signals and server 106 may determine the presence of the object in the excited state.

As noted, FIGS. 6A and 6B depict aspects of example computing devices in accordance with one or more example embodiments. FIG. 6A depicts aspects of a computing device in accordance with one or more example embodiments. In FIG. 6A, scenario 600 provides a computing device 602 that may be positioned adjacent to medium 604. In some instances, computing device 602 may be similar as computing device 102A in FIGS. 1 and 2. Yet, further, computing device 602 may be configured to communicate with other computing devices, such as another computing device described in further detail in FIG. 6B.

In some embodiments, medium 604 may be part of a human body or an organ encompassing object 610. Further, object 610 may be a kidney stone that may be 1 to 15 mm in diameter and medium 604 may be a kidney. In other embodiments, object 610 may be a foreign object (e.g., a bullet from a handgun, a catheter, or a stent), a gall stone, a salivary duct stone, tissue, a blood vessel, plaque, and/or a bone fragment, among other possibilities. Yet further, in some instances, object 610 may be a mass or a buildup of minerals, such as a concretion, for example. Other examples of mediums and objects may exist.

In some embodiments, object 610 may include reflection items that may be used to help detect the presence of object 610 in medium 604. In some instances, reflection items may include a bubble, a calcification, a crevice, a crack, and/or a concretion associated with the object. For example, a reflection item may be bubble 612 on object 610. In some instances, bubble 612 may be in a crack and/or crevice of object 610. As a general matter, it should be noted that bubbles may also be formed in free fluid, concretions, and/or tissues in a mammal. For example, bubble 610 may be formed on any of the example objects described above for object 610. Further, in some instances, a bubble, such as bubble 612, may include trapped air, a gas pocket, and/or air emboli. In addition, bubble 612 may be stationary or in motion while on the surface of object 610.

It should be noted that bubble 612 is illustrated in FIG. 6A as a growing bubble. As shown, the dotted lines in FIG. 6A illustrate that bubble 612 has grows from a smaller bubble to the current size illustrated by the solid line surrounding the dotted lines. In particular, the dotted lines may resemble the outer surface of bubble 612 as it grows. As such, it should be understood that detection signals may interact with bubble 612, causing it to grow. In addition, it should be also noted that detection signals may interact with bubble 612 to drive it into instability. For example, the detection signals may vary the size and/or shape of bubble 612 and change the properties of bubble 612 to detect the reflective properties of bubble 612, as described further with respect to block 506 of FIG. 5.

FIG. 6B depicts aspects of another computing device in accordance with one or more example embodiments. In FIG. 6B, scenario 650 provides a computing device 660 that may be positioned adjacent to medium 664. In some instances, computing device 660 may be similar to computing device 102A and/or computing device 602. In FIG. 6B, medium 664 may be a human body or the body of some other living mammal. As a general matter, object 670 may be similar to object 610 and bubble 672 may be similar to bubble 612. For example, bubble 672 may also be a growing bubble. Further, object 670 may be a kidney stone that is 5-12 mm in diameter with reflection items to detect the presence of object 670 in medium 664.

a. Produce One or More Detection Signals

As noted for block 502 of FIG. 5, a computing device may carry out functions for producing one or more detection signals configured to induce an excited state of an object. As illustrated in FIG. 6A, computing device 602 may produce detection signals. For example, computing device 602 may produce pulses in a direction 606 toward medium 604 and object 610. In some instances, computing device 602 may produce pulses that penetrate the surface of medium 604 and reflect off of object 610. Further, computing device 602 may increase or decrease the amplitude of detection signals to interact with bubble 612 on object 610 and induce an excited state of object 610. As noted, the detection signals may drive bubble 612 into oscillation and/or instability.

In some embodiments, computing device 602 may produce detection signals that are focused on a region of object. In some instances, detection signals may be focused on a reflection item. For example, computing device 602 may produce detection signals focused or directed to bubble 612. For instance, referring back to FIG. 2, detection signals may be focused or directed toward a given bubble by positioning probe 214 in a given manner. In some instances, probe 214 may be angled in such a way to direct detection signals towards the given bubble. As such, the detection signals may be focused on the left side of bubble 612. In some instances, detection signals may be directed towards the left side of bubble 612 and then the signals may be directed towards to the right side of bubble 612. Other possibilities may also exist.

Figure 6C:
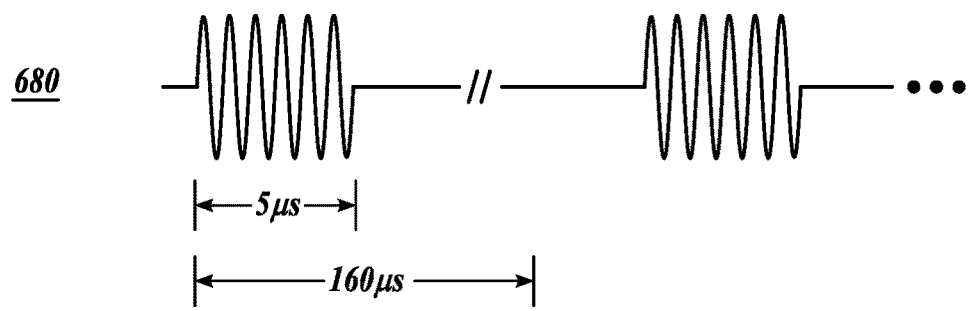
FIG. 6C depicts aspects of signals produced from the computing devices in FIGS. 6A and 6B in accordance with one or more example embodiments.
Figure 6C:
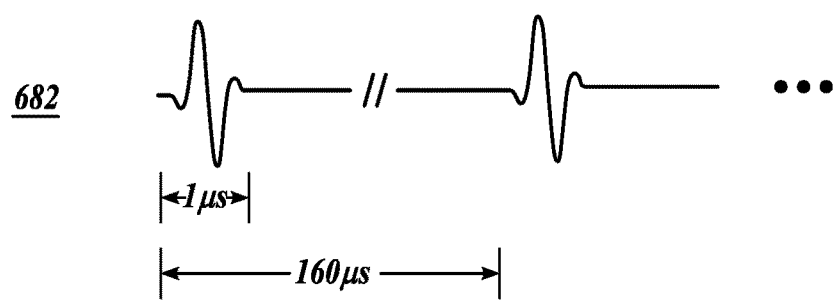
Figure 6C:
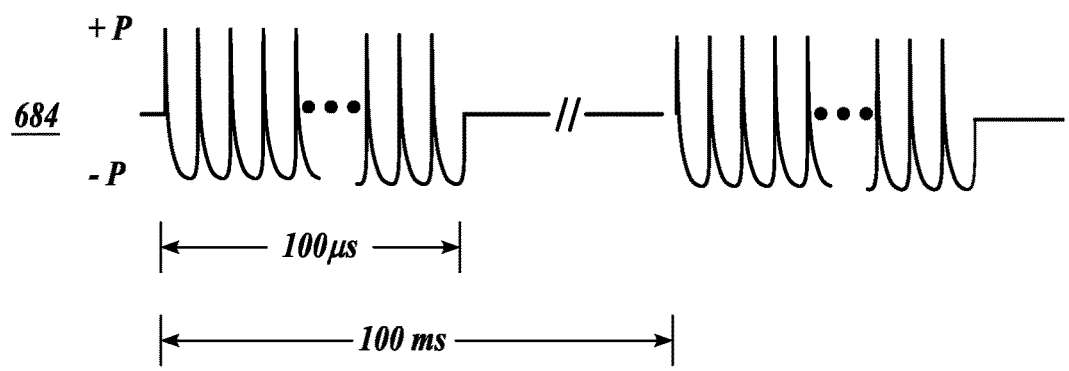
Figure 6C:
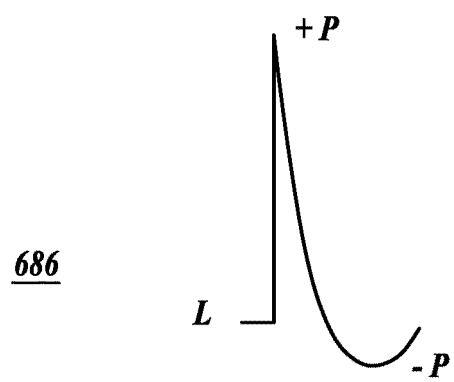

In some embodiments, computing devices 602 and 660 may produce different types of detection signals. FIG. 6C depicts aspects of signals produced from the computing devices 602 and 660 in FIGS. 6A and 6B, respectively, in accordance with one or more example embodiments. In FIG. 6C, signal 680 may be a Doppler signal with a multiple pulses. Further, signal 682 may be a B-mode with plane waves. Yet further, signal 684 may be a pulse sequence with peak positive pressures (P+) and peak negative pressures (P−). In addition, signal 686 may be a shock wave pulse.

As a general matter, detection signals may include one or more bursts such that each burst includes a number of pulses. For example, as illustrated by signal 680, a single burst may include 14 pulses. It should be noted that signal 680 may also have one or more of cycles such that each cycle includes a burst and a time period before or after the burst. In particular, signal 680 may have a 160 microsecond cycle with a burst of 5 microseconds. As such, 155 microseconds may be a time period after the burst. It should be noted that detection signals may include a range of 7 to 21 bursts. Yet further, detection signals may include 2 to 7 cycles of bursts and time periods without bursts.

In some instances, various modes may be employed by computing devices 602 and 606 to produce the detection signals. For example, Doppler mode may be used produce signal 680. As noted above, signal 680 may include 14 identical pulses such that the pulses are produced consecutively by a probe and/or a transducer (such as probe 214). It should be noted that Doppler mode may be implemented to produce the 14 pulses in signal 680. In some instances, such pulses may be produced with a 3 kHz pulse-repetition frequency (PRF). Further, the PRF may be adjusted and/or modified according to the dimensions of object 610 and/or bubble 612. It should be noted that signal 680 may have varying amplitudes to provide an initial excitation pulse with greater amplitudes followed by lower amplitude pulses.

In some instances, B-mode may be used to produce signal 682. As noted above, signal 682 may include a series of plane waves. In some instances, signal 682 may include a one micro-second plane wave in a 160 micro-second cycle. It should be understood that B-mode may be implemented to produce the plane waves in signal 682. Further, in some instances, a Push mode may produce signal 684. As illustrated, signal 684 may include a 3 millisecond cycle with a burst of pulses over a 100 microseconds.

Yet further, in some instances, a Shock mode may produce 686. Signal 686 may have characteristics similar, in some respects, to signals produced by lithotripters for breaking up object 610. However, it should be understood that computing devices 602 and 606 are not the same as conventional lithotripters. As described above, computing device 602 and 606 may produce a variety of different signals, including those produced by lithotripters.

In some embodiments, detection signals may include pressure waveforms, possibly excitation signals and/or pulses. As noted, signal 684 may have positive pressures (P+) and negative pressures (P−) of pressure waveforms. In some instances, signal 684 may also be re-produced in three cycles and a central frequency of 5 MHz. In some instances, positive pressures and negative pressures of signal 684 may be 2 MPa and −1 MPa, respectively. As such, signal 684 may excite object 670 such that bubble 672 in and/or on object 670 grows with each signal interacting with bubble 672. It should be noted that the positive and negative pressures of signals 684 may be adjusted. In particular, the pressures may be raised to drive bubble 672 into oscillation. Further, in some instances, the pressures may be lowered to prevent saturation of the oscillation effect.

In some embodiments, a variation of the different signals may be produced. For example, signal 684 may be produced to interact with bubble 672, possibly driving bubble 672 into oscillation. In addition, signal 680 may be produced and reflection signals may be received to indicate the presence of object 670. In particular, the reflection signals may include phase variations or phase variability indicative of the presence of object 670. Thus, as further described below for block 506 of FIG. 5, the presence of object 670 may be determined. In some instances, signal 686 may be produced to break object 670 into fragments. As such, signal 684 may be produced to oscillate bubbles on object 670 and signal 680 may be produced to receive reflection signals indicative of the presence of object 670. Other possibilities may also exist.

In some embodiments, detection signals may be produced and directed to a human body. For example, referring back to FIG. 6B, computing device 660 may produce detection signals in a direction 666 toward medium 664 and object 670. In some instances, computing device 660 may produce pulses that penetrate the surface of medium 664 to reflect off of object 670, possibly returning in a direction 668 toward computing device 660.

As noted, detection signals may be configured to induce an excited state of an object. For example, computing device 660 may produce detection signals configured to induce an excited state of object 670. In some instances, computing device 660 may produce amplified signals that interact stochastically with bubble 672 on object 670, possibly driving bubble 672 into oscillation. It should be noted that detection signals with certain characteristics described above may excite object 670. For example, the negative pressure phases of the detection signals produced by computing device 660 may induce an excited state of object 670. In particular, negative pressure phases may create tension that oscillates bubble 672.

In some instances, bubble 672 may be in the bulk of object 670 and/or on the surface of object 670. As such, detection signals may excite bubble 672 in the bulk of object 670 or cracks inside object 670. In some instances, detection signals may interact with internal calcifications in object 670 to produce an excited state of object 670. In other instances, detection signals may excite bubble 672 on the surface of object 670, particularly if there are microscopic crevices on the surface of object 670. In particular, detection signals may induce an excited state of object 670 when there are gas pockets on the surface of object 670. It should be noted that bubbles such as bubble 672 may be micron or submicron size so as to be invisible and detectable only by inducing the excited state of object 670.

b. Receive One or More Reflection Signals

As noted for block 504 of FIG. 5, the computing device receives one or more reflection signals, where the reflection signals correspond to at least one of the detection signals reflected from the object. As noted for FIG. 6A, computing device 602 may produce detection signals in a direction 606 toward medium 604 and object 610. The reflected signals may return in a direction 608 toward computing device 602 so as to be received by computing device 602. In some instances, computing device 602 may be placed 5-15 centimeters away from medium 604 when sending and receiving pulses and in other instances, computing device 602 may be farther away from, or closer to, medium 604. In other instances, computing device 602 may make contact with the outer surface of medium 604 when sending and receiving pulses.

In a similar manner, FIG. 6B illustrates reflected signals returning in a direction 668 toward computing device 660. Further, reflection signals may indicate the presence of bubble 672, possibly indicating the presence of object 670. It should be noted that one or more pressure waveforms produced by computing device 660 may be measured by a hydrophone associated with computing device 660, possibly integrated within computing device 660. In other instances, the waveforms produced by computing device 660 may be measured by a broadband hydrophone having a sensitivity of 48 nV/PA at 5 MHz.

c. Determine a Presence of an Object

As noted for block 506 of FIG. 5, based on the received one or more reflection signals, the computing device determines a presence of the object in the excited state. As noted for FIGS. 6A and 6B, computing devices 602 and 660 may receive reflection signals after exciting bubbles 612 and 672, respectively.

As a general matter, computing devices may determine the presence of exited object by analyzing the reflection signals. As noted above, reflection signals from an excited object may have different characteristics than signals reflected from objects that are not excited. Such differences may help, facilitate, and/or aid in detecting the excited object. In particular, various measurements of the reflection signals may indicate the presence of an excited object. For example, a variance in the reflection signals may be measured to determine the excited object. In further examples, bubbles may be driven into oscillation and the oscillation may be determined by measuring phase variability, amplitude, and/or harmonics associated with the reflection signals. Thus, by determining the oscillation, the presence of the object and/or the bubble in the excited state may be determined. Additional examples of determining an object in the excited state are described below.

Figure 7A:
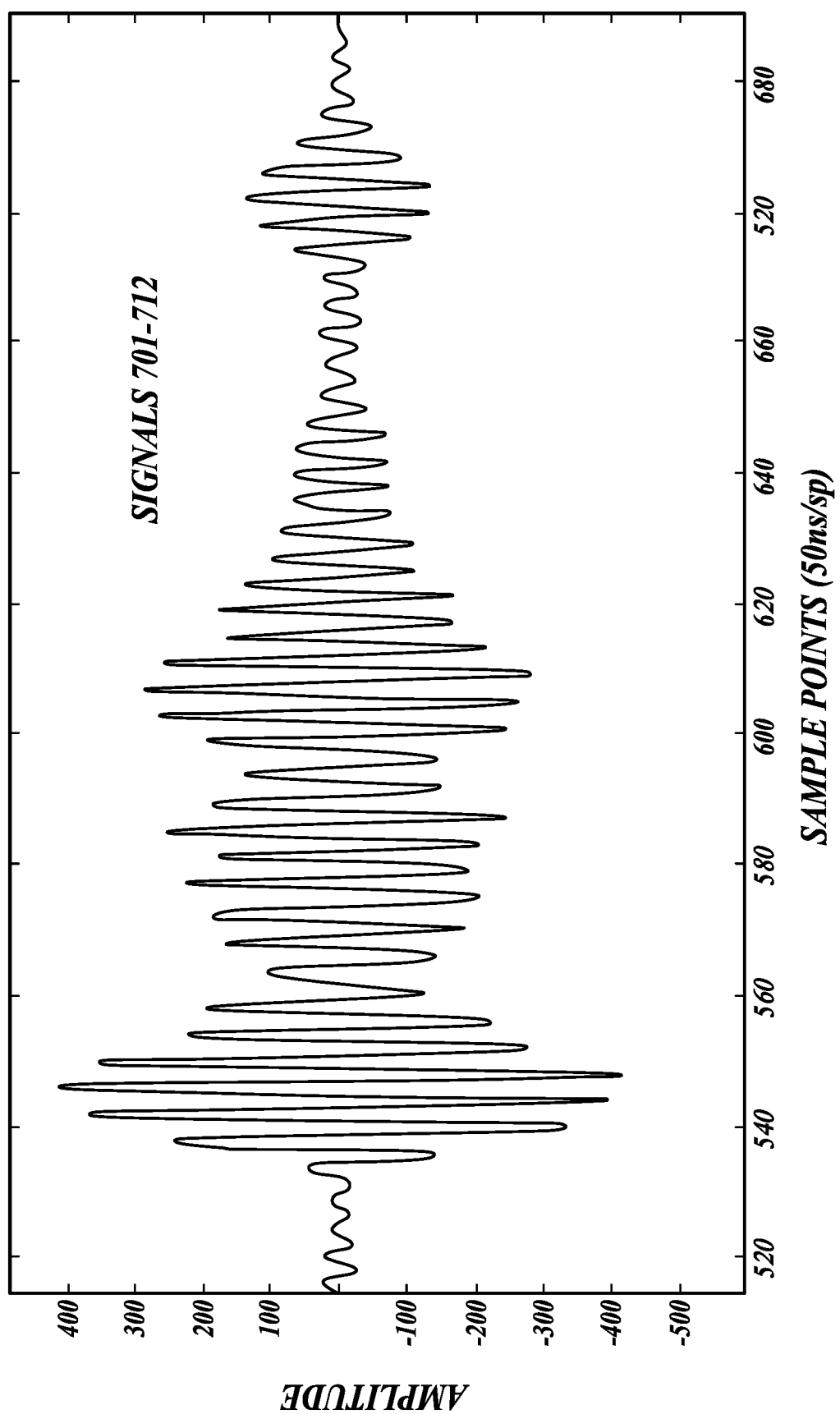
FIG. 7A depicts aspects of reflection signals associated with a computing device in accordance with one or more example embodiments.

In some embodiments, an object in the excited state may be determined by analyzing reflection signals. FIG. 7A depicts aspects of reflection signals associated with a computing device in accordance with one or more example embodiments. Further, FIG. 7A may illustrate reflection signals including 12 signals, signals 701-712. For example, signals 701-712 may be reflection signals reflected from an excited object and received by a computing device. The signals may be measured by amplitude on the y-axis and time on the x-axis, with sample rate of 50 nanoseconds per sampling point. As illustrated, signals 701-712 may be represented on the same graph in FIG. 7A such that each signal overlaps one another. It should be noted that signals 701-712 may have similar characteristics such that overlapping the signals over one another creates the appearance of a single signal in FIG. 7A.

Figure 7B:
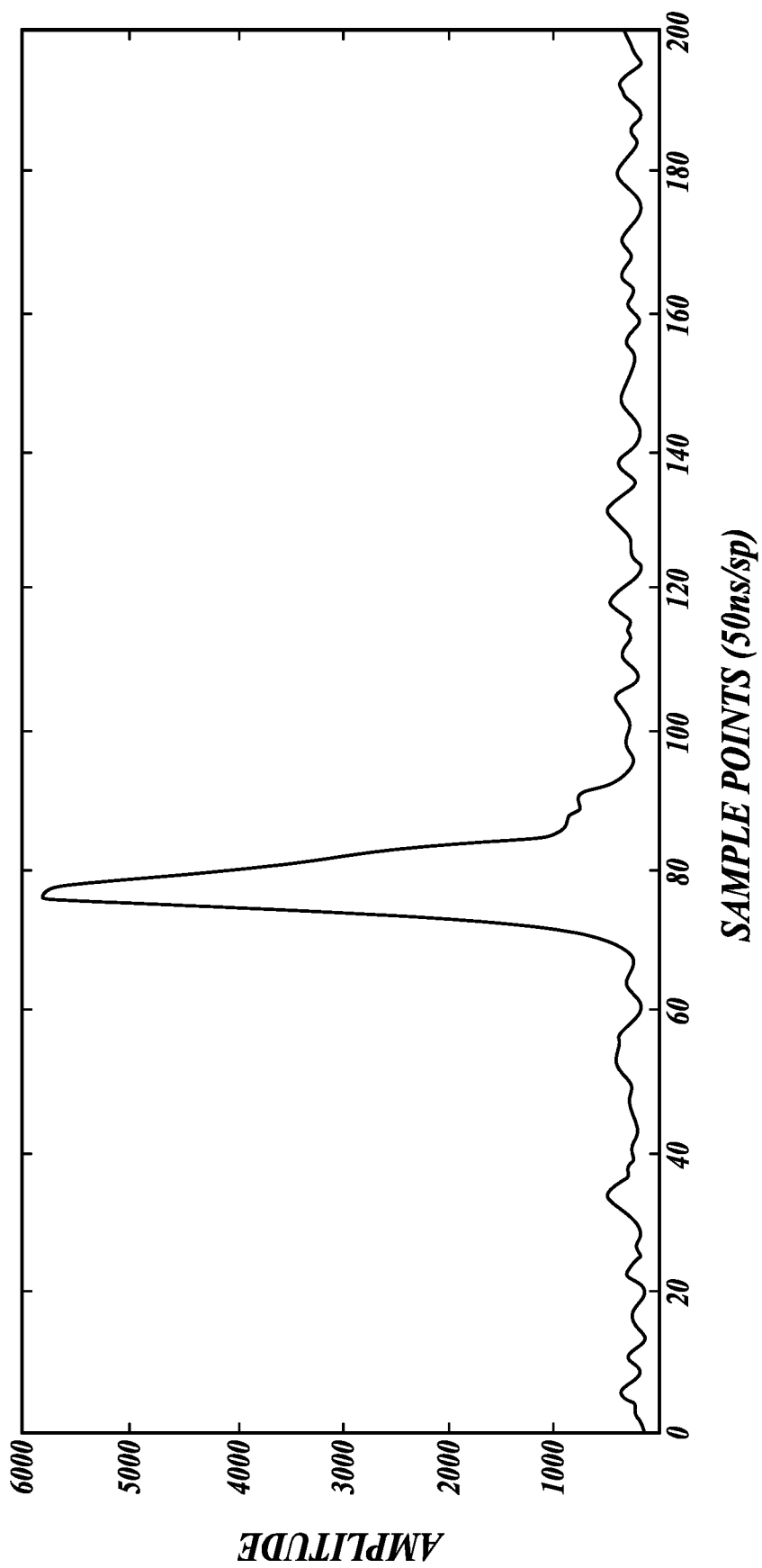
FIG. 7B depicts aspects of signals indicative of an object in accordance with one or more example embodiments.

In some embodiments, the power of signals may be used to determine the presence of the excited object. As one example, Doppler power calculated from Doppler signals may be used to identify an object. FIG. 7B depicts aspects of signals indicative of an excited object in accordance with one or more example embodiments. In particular, FIG. 7B illustrates the power of the signals illustrated in FIG. 7A. Further, FIG. 7B illustrates Doppler power calculated on a decibel scale (dB) on the y-axis and time on the x-axis, with a sampling rate of 50 nanoseconds per sampling point.

As illustrated in FIG. 7B, a spike in the data occurs approximately 2-3 microseconds after receiving signals reflected off the excited object. In some instances, such spikes indicate that portions of pulses in FIG. 7A fluctuate from pulse to pulse. Such spikes in power, or fluctuations from pulse to pulse, may be used to determine the presence of an excited object. It should be noted that the Doppler power may be calculated relative to the background noise level.

Figure 7C:
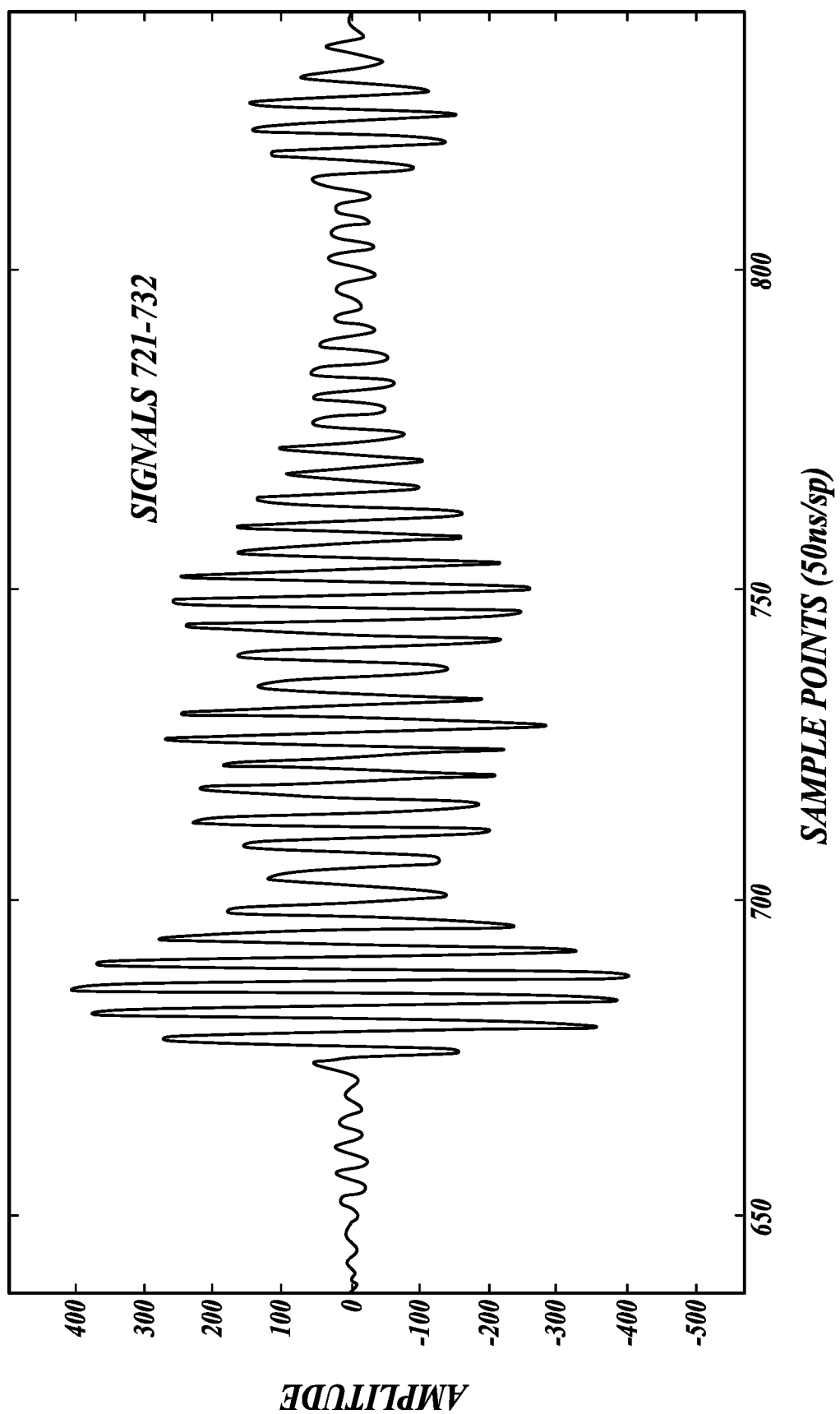
FIG. 7C depicts aspects of artificial signals that simulate the reflection signals in FIG. 7A in accordance with one or more example embodiments.

In some embodiments, computing devices 602 and 660 may determine that an excited object is not present. For example, computing devices may make such determinations based on receiving artificial signals simulating those of reflection signals. For example, FIG. 7C depicts aspects of artificial signals that simulate the reflection signals in FIG. 7A in accordance with one or more example embodiments. Further, FIG. 7C may illustrate artificial signals including 12 signals, signals 721-732. For example, signals 721-732 may be produced by a waveform generator and received by a computing device. The signals may be measured by amplitude on the y-axis and time on the x-axis, with sample points at 50 nanoseconds per sampling point. As illustrated, signals 721-732 may be represented on the same graph in FIG. 7C such that each signal overlaps one another. It should be noted that signals 721-732 may have similar characteristics such that overlapping the signals over one another creates the appearance of a single signal in FIG. 7C. It should be noted that signals 721-732 may be produced using a mathematical modeling software and a function generator.

Figure 7D:
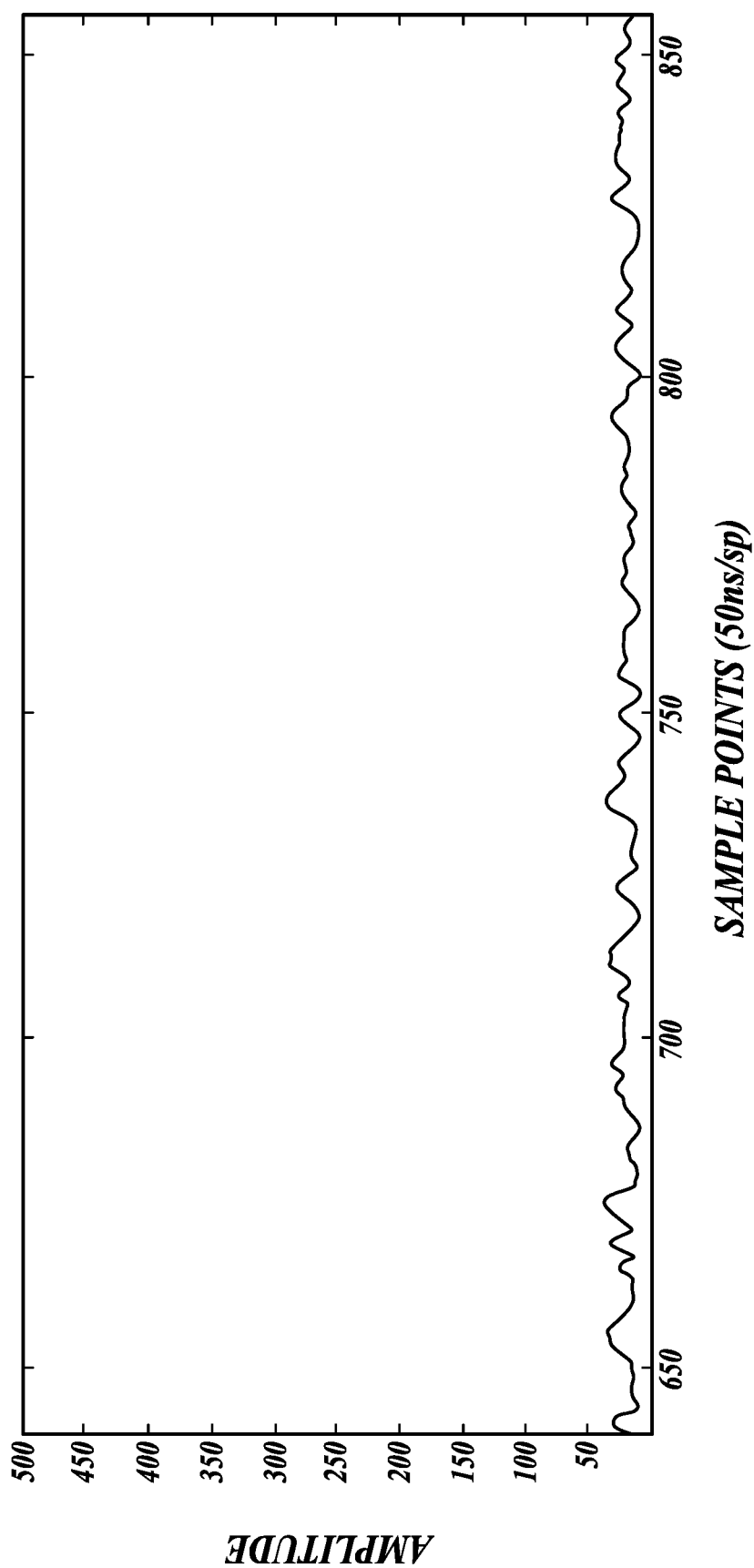
FIG. 7D depicts aspects of different signals than the signals in FIG. 7B in accordance with one or more example embodiments.

FIG. 7D depicts aspects of different signals than those in FIG. 7B in accordance with one or more example embodiments. In particular, FIG. 7D illustrates the power of the simulated signals illustrated in FIG. 7C. Similar to FIG. 7B, FIG. 7D illustrates Doppler power calculated on a decibel scale (dB) on the y-axis and time on the x-axis. Further, the Doppler power may also be calculated relative to the background noise level. As illustrated, there is no spike in the data after receiving the simulated signals in FIG. 7C. Therefore, no excited objects are detected from the simulated pulses of FIG. 7C. Instead, excited objects may only be detected from reflection signals reflected from the excited object and received by the computing device.

In some embodiments, an excited object may be detected without signal processing. Recall that FIG. 7B illustrates detecting the excited object without signal processing. In particular, FIG. 7B illustrates the excited object based on signals output from an analog-to-digital converter (ADC) of the computing device, possibly ADC 216 in FIG. 2. Moreover, the excited object may be based on raw RF data from ADC 216 and not from signal processing of the RF data. Since FIG. 7B illustrates an excited object and FIG. 7D does not, the excited object may be detected from reflection signals (e.g., raw RF data) and not from artificial signals mimicking reflection signals. Thus, in such instances, the excited object may be identified solely by the RF data signals received by the computing device, without any signal processing of the reflection signals.

In some embodiments, various modes for producing detection signals may be used to determine an excited object. For example, referring back to FIG. 6A-6C, computing devices may determine the presence of an object using the various modes for producing the detection signals. As noted, Doppler mode and B-mode may be employed to produce detection signals. Based on such modes, reflection signals may be received and processed accordingly by the analog-to-digital converter, such as ADC 216. Further, such signals may determine a presence of object 610 in the excited state. In some instances, digital signals output from the ADC 216 may further be filtered, amplified, and/or clipped through further signal processing and the presence of excited object 610 may be determined.

Figure 8A:
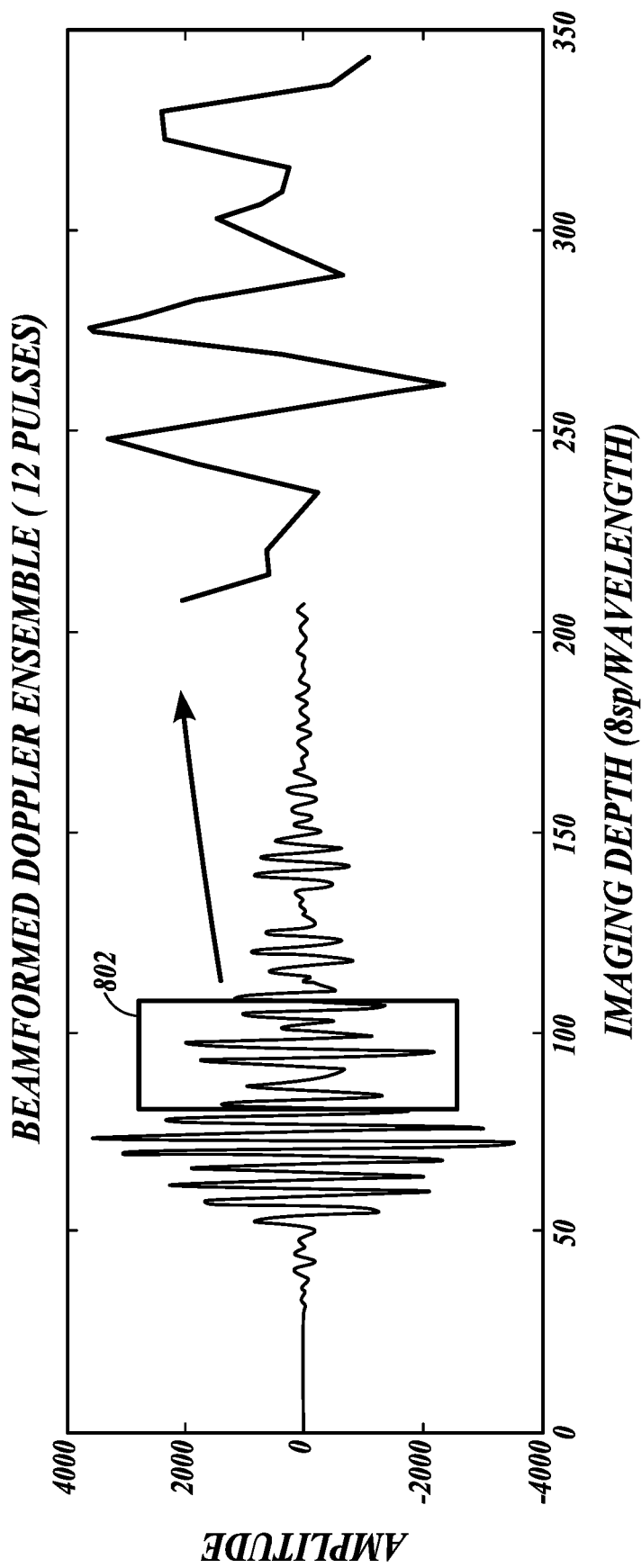
FIG. 8A depicts aspects of Beamformed Doppler pulses in accordance with one or more example embodiments.
Figure 8B:
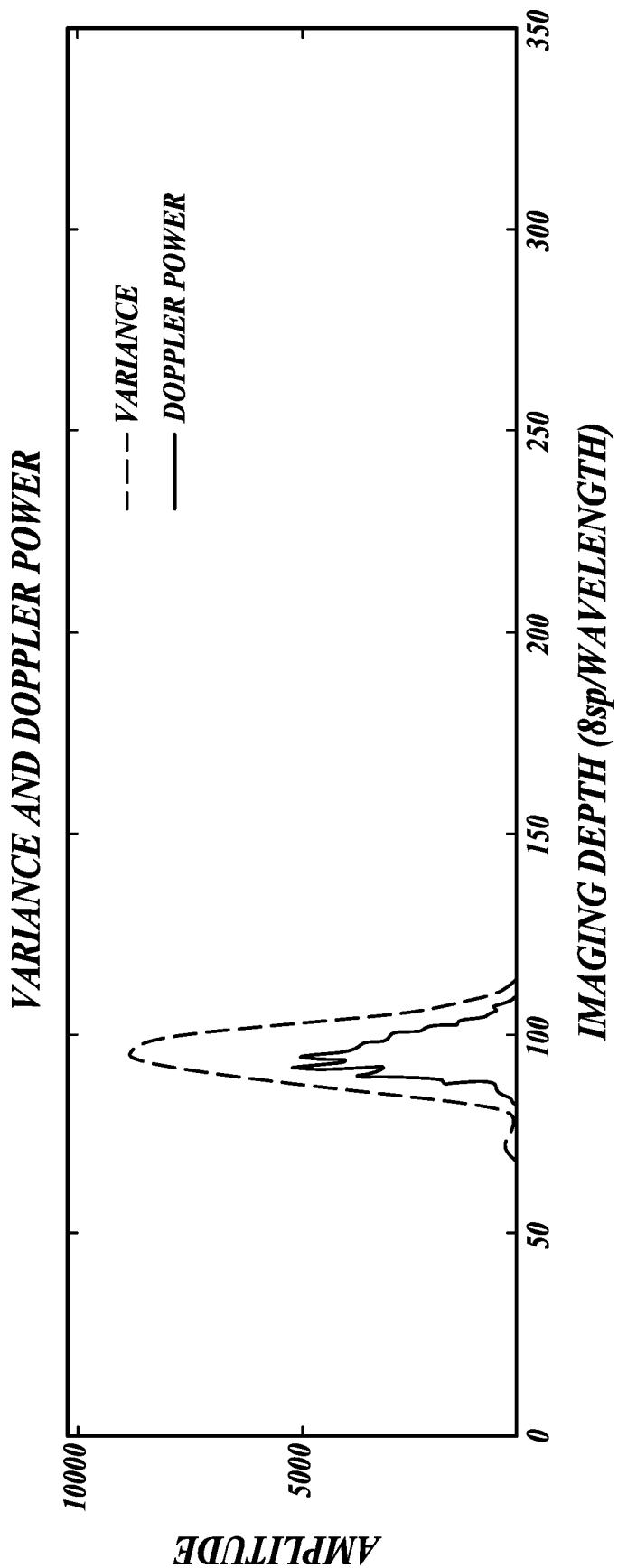
FIG. 8B depicts aspects of a variance and Doppler power in accordance with one or more example embodiments.

In some embodiments, spikes in amplitude of reflection signals may be used to determine an excited object. For example, FIG. 8A depicts aspects of Beamformed Doppler pulses in accordance with one or more example embodiments. Further, FIG. 8B depicts aspects of a variance (e.g., phase variability of one or more reflection signals) and Doppler power in accordance with one or more example embodiments. As illustrated, residual amplitudes may be measured on the y-axis and imaging depth may be measured on the x-axis. As shown in FIG. 8A, residual amplitudes may vary from pulse to pulse. For instance, some pulses in area 802 show spikes in residual amplitude which occur at the same depth as the spike in the corresponding Doppler power, indicating the presence of an excited object. As illustrated, area 802 of FIG. 8A corresponds to the spike in the Doppler power in FIG. 8B for detecting an excited object. It should also be noted that the variance may determine the presence of the excited object.

In some embodiments, the Doppler power may be calculated based on the residual amplitude. As such, the Doppler power may be calculated to determine the presence of an excited object. For example, the residual amplitude $A_{nm}$, may be calculated for each Doppler pulse within a series of Doppler pulses. Further, Doppler power $W_m$ may be calculated by the following equation:

$$W_m = \frac{1}{N}\sum_{n=1}^{N} A_{nm}^2$$

As such, calculating the Doppler power using the equation above may determine the presence of an excited object found in a given medium.

Figure 9:
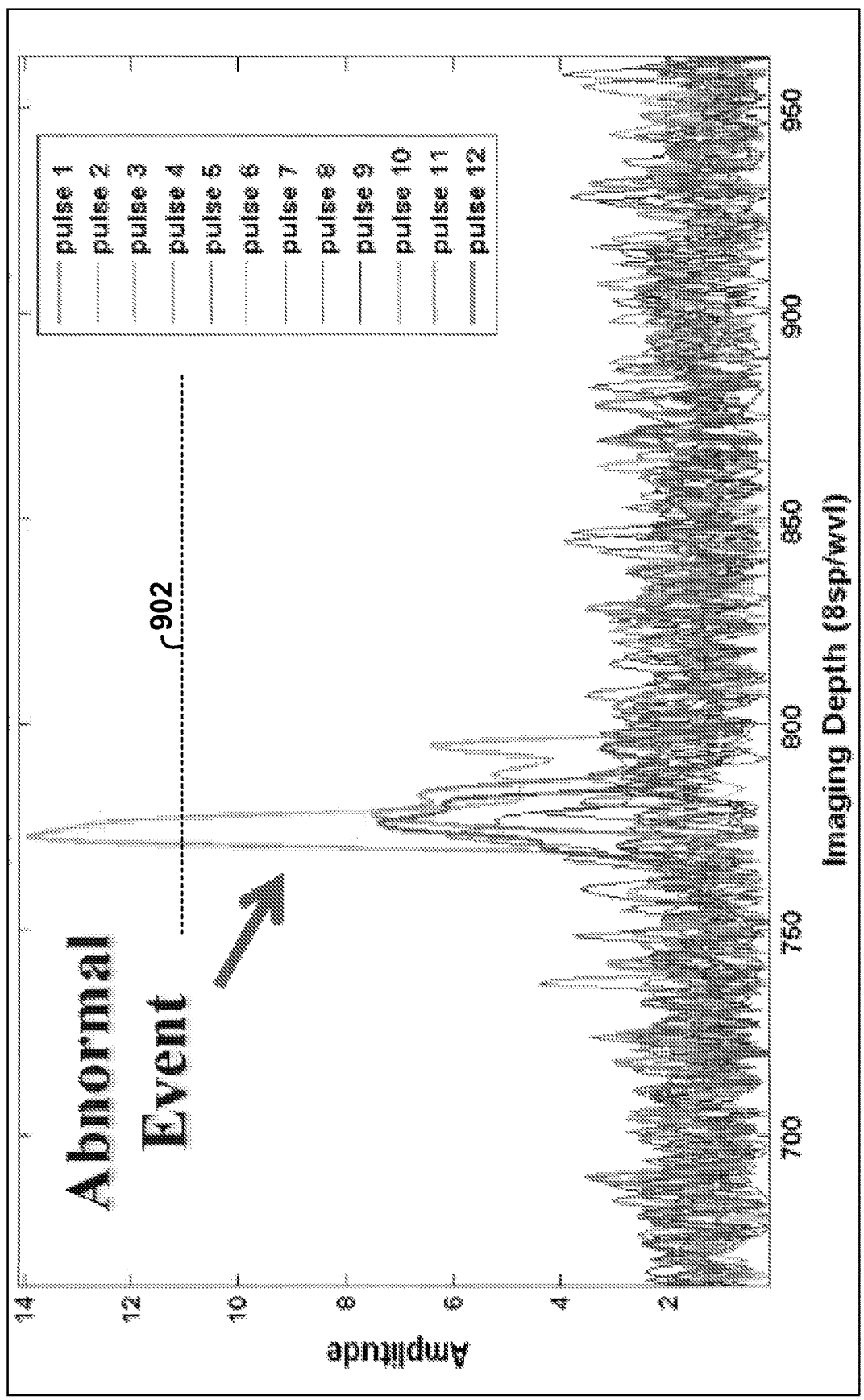
FIG. 9 depicts aspects of an abnormal event in accordance with one or more example embodiments.

In some embodiments, the appearance of a spike in residual amplitude may be considered an "abnormal event," indicating the presence of an excited object. To determine an abnormal event, a maximum residual amplitude or a threshold amplitude may be determined for reflection signals. For example, the maximum residual amplitude for a series of pulses may be 3 dB over the averaged maximum residual amplitude for the series of pulses. FIG. 9 depicts aspects of an abnormal event in accordance with one or more example embodiments. As illustrated in FIG. 9, the amplitudes of twelve pulses are measured on the y-axis and the imaging depth is measured on the x-axis. The distribution of the amplitude may show that the abnormal event appears uniformly over all the pulses in the series of pulses, indicating the presence of an excited object.

In some embodiments, a threshold may be applied to determine the presence of an excited object. For example, as illustrated in FIG. 9, threshold 902 may be applied to the amplitudes in FIG. 9. In particular, an amplitude that exceeds threshold 902 may determine the presence of an excited object. It should be noted that thresholds, such as threshold 902, may be applied to FIGS. 7B, 8A, and 8B in a similar manner to determine an excited object. In addition, it should be understood that thresholds may not be linear as shown with threshold 902. In particular, thresholds may take the form of a function and may also change dynamically with respect to different signals and amplitudes.

In some embodiments, signal processing may be used to display an image of the excited object. For example, B-mode images combined with Doppler-mode images may be generated to display an excited object. Further, such images may be generated using signal processing algorithms that utilize Doppler thresholds. For instance, color information of reflected signals may be based on a comparison between the Doppler power of reflected signals and a Doppler power threshold or a maximum Doppler power. In some instances, the maximum Doppler power may be decreased to a minimum level (e.g., a level just above the level background noise.) Further, color-write priority may be set to the highest level such that color information, rather than the B-mode information, may always be plotted on a graphical display. Further examples of displaying an excited object is described for block 508 of FIG. 5 below.

In some embodiments, signal processing may involve a numerical computation environment to determine the presence of an excited object. For analyzing reflection signals of an excited object, the signal processing may be based on mathematical codes and/or computational algorithms. In particular, characteristics of reflection signals may be calculated and these characteristics may indicate a presence of the excited object. For example, the Doppler residual and Doppler power may be characteristics that may be calculated by a numerical computation environment to determine an excited object.

In some embodiments, pulses of the reflection signals may be analyzed to determine the presence of an excited object. For example, consider a signal $U_n(t)$, n=1, 2, . . . , N, where N pulses represent reflections signals in the form of a series of pulses received by a computing device. For purposes of illustration, consider N=12 such that there are twelve pulses in each series of pulses. However, it should be noted that a general Doppler series may include fourteen pulses. In some instances, a Doppler shift may be measured by the following equation:

$U_n(t-nT)$, for different $n$ pulses, where

T=1/pulse-repetition frequency (PRF), and where T is the period for the series of pulses.

As such, a Doppler shift may be indicative of the presence of an excited object. Yet further, the Doppler shift may be related to phase variability also giving rise the presence of an excited object.

In some instances, reflected signals may be received uniformly and no Doppler shift may be determined. However, any differences from pulse to pulse may be determined in the above-referenced equation, possibly determining the presence of an excited object. For instance, $U_n((t-nT)$ for different n pulses, may indicate pulses reflecting off an object and arriving to the computing device with a time shift. Further, a velocity of an object may be calculated from the time shift, possibly indicating the presence of an excited object. Yet further, in some instances, $U_n(t)$ may not indicate the time shift, but may instead indicate a fluctuation based on the reflections signals. In such instances, a velocity of the object may also be calculated such that the presence of the excited object may be determined.

In some embodiments, additional signal processing may be implemented to determine the presence of an excited object. For example, after analog-to-digital conversion, the signal, $U_n(t)$, may be transformed to digital signals characterized by the following equation:

$U_{nm}=U_n(t_m-m\Delta T)$, where $\Delta t$ is the signal sampling step (e.g., 50 ns for a 20 MHz sampling frequency), and where m=1, 2, ... M, and where M is the total number of samples recorded in one period of a Doppler series.

In some instances, M=1024 but it should be noted that M may be other values as well. In some instances, beamformed signals may be calculated and processed for each channel. Such signals may be formed by a "delay-and-sum" beamforming method. For example, consider $U_{nm}$, the digitized signal for either non-beamformed or beamformed channel data. In some instances, signal processing of the channel data may calculate the quadrature components of the signals $U_{nm}$. Further, calculating the quadrature components of the signals $U_{nm}$ may involve using the Hilbert transform. The Hilbert transform may be made using real-time mathematical software platforms such that Q=Hilbert (U). As a result, for each of the n pulses, a complex ("analytic") signal may be characterized by the following equation:

$V_{nm}=U_{nm}+iQ_{nm}$, where the quadrature signal, $Q_{nm}$, is the Hilbert transform of $U_{nm}$ and i is an imaginary unit.

As such, the analytic signal may be used to determine the presence of an excited object through additional signal processing.

In some embodiments, "wall filtering" may be used to determine a presence of an excited object. In some instances, wall filter may be used to reduce signal fluctuations of the reflection signals, possibly due to slow-moving reflection signals. For example, a first order regression filter may be applied to the analytic signal $V_{nm}$. In particular, for each fast time-moment m, the corresponding signals from different pulses within the reflection signals may be considered as a function of the n pulses. For example, for the n pulses and the function may characterized as a linear expression:

$V_{nm}=a_m+n\ b_m$.

The expression may provide for $V_{nm}$ using a least squares estimation (where $a_m$ and $b_m$ may be some coefficients that do not depend on the pulse number n.) Further, the residual signal may be the wall-filtered signal, $\acute{V}_{nm}=\vec{V}_{nm}-\nabla_{nm}$. Yet further, the absolute value of that signal may be the residual amplitude, $A_{nm}=|\tilde{V}nm|$. Thus, $A_{nm}$ may be used to detect fluctuations in the reflection signals to determine the presence of an excited object. Further, the average power may provide the Doppler power at the time $t_m=m\Delta t$ using the following equation.

$$W_m = \frac{1}{N}\sum_{n=1}^{N} |\tilde{V}nm| \wedge 2$$

As noted, calculating the Doppler power may determine the presences of an excited object found in a given medium.

In some embodiments, it may be possible to distribute aspects or individual steps for determining the presence of the object in the excited state. For example, referring back to FIG. 6B, computing device 660 may send detection signals and receive reflection signals from excited object 670. Further, computing device 660 may communicate with server 652 through communication link 658 such that server 652 may determine the excited object (e.g., determining the Doppler power of the reflection signals). In addition, server 652 may communicate with computer 656 through communication link 654 such that server 652 and computer 656 may share processes for determining the excited object. In some instances, computing device 660 may communicate with computer 656 through communication link 662 such that computer 656 may determine the excited object (e.g., provide a graphical display of the Doppler power). Other possibilities may also exist.

It should be noted that communication links 658, 654, and 662 may be physically wired communication links such as serial bus connections and/or parallel bus connections. Alternatively, these communication links may be wireless communications, e.g., Bluetooth® radio technology, Cellular technology (such as GSM, CDMA, or WiMAX), or Zigbee® technology, among other possibilities.

d. Cause an Output Device to Provide an Indication

As noted for block 508 of FIG. 5, the computing device causes an output device to provide an indication of the presence of the object in the excited state. In some embodiments, a computing device may communicate with one or more other computing devices to display an indication of the object in the excited state.

In some embodiments, computing device 660 may communicate with computer 656 to display characteristics of object 670. Further, computer 656 may display data indicative of the material surrounding object 670, the size of object 670, the position of object 670 (e.g., coordinates in a three-dimensional layout), among other possibilities. As such, computer 656 may provide information indicating of the presence of object 670 in medium 664. As described in further detail herein, computer 656 may provide graphical representations indicating the presence of object 670 in medium 664. In some instances, computer 656 may display a harmonic image of object 670 in the excited state. Further, computer 656 may include a speaker to generate an audible sound corresponding to one or more detection signals, possibly indicative of detecting object 670.

It should be noted that although computer 656 is illustrated as a laptop computer, computer 656 may also be a smaller computing device such as network-access device 102D, for example. Yet further, it should be noted that various embodiments described herein may be combined or interchangeable. For example, a smaller version of the graphical display on computer 656 may be incorporated with computing device 660 to display the characteristics of object 670 and to detect the presence of object 670. Other possibilities may also exist.

4. ADDITIONAL FEATURES AND FUNCTIONS

In some embodiments, a pressure within a medium encompassing the object may be determined. In some instances, determining the pressure of the medium may aid, facilitate, and/or help to detect the object within the medium. For example, reducing the static pressure in the medium may help to reduce any suppression of twinkling or excitation such that the object may be detected. It should be noted that the examples below are provided for purposes of illustration and should not be interpreted as limiting. For example, one or more of the processes, methods, and/or functions below may be performed or similarly performed on a mammal, such as a human.

Figure 10:
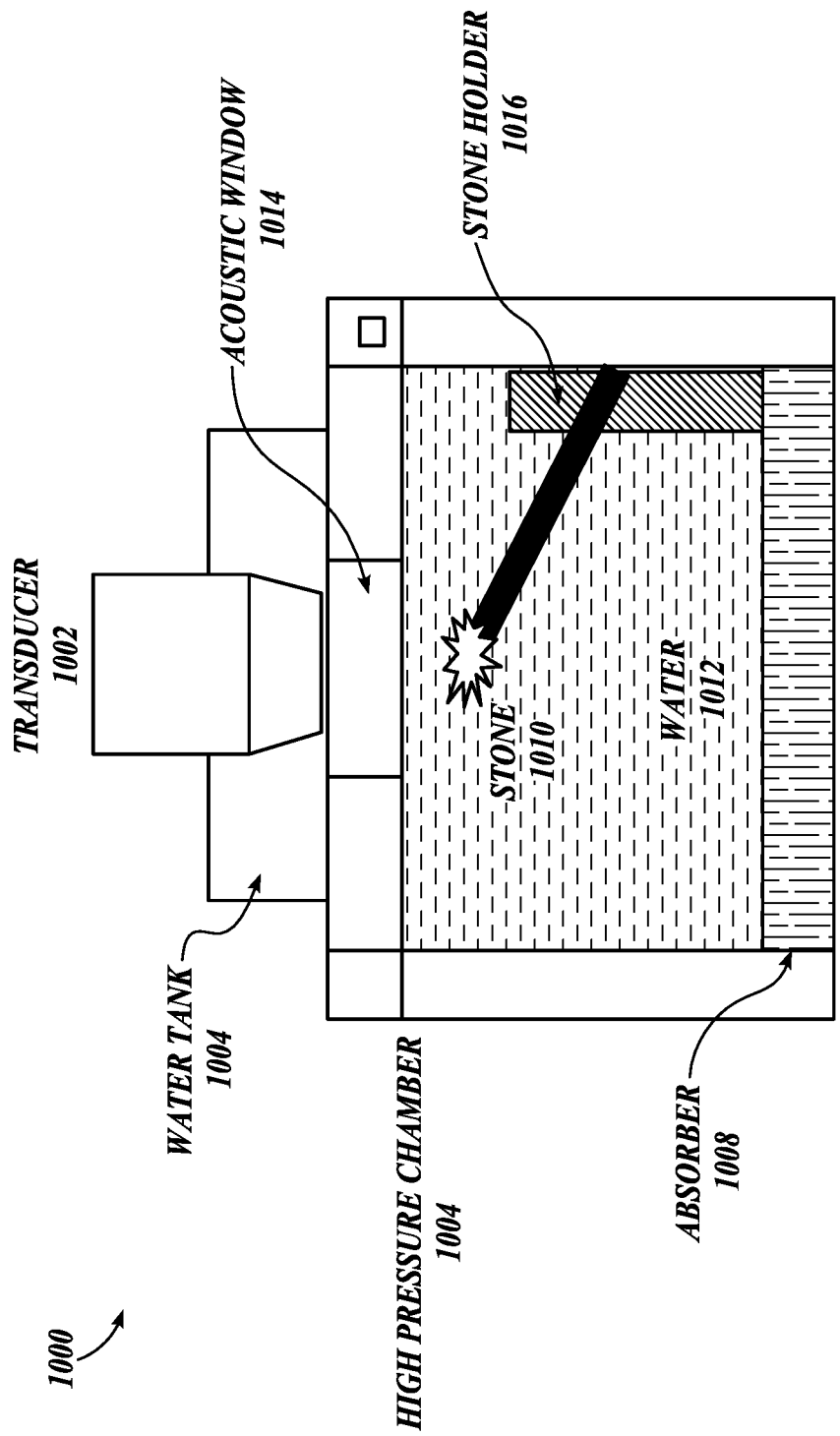
FIG. 10 depicts aspects of monitoring pressure of a medium in accordance with one or more example embodiments.

FIG. 10 illustrates monitoring pressure of a medium, according to an example embodiment. In FIG. 10, transducer 1002 (e.g., a probe) may be placed in water tank 1004 and above high pressure chamber 1004. It should be noted that transducer 1002 may be the same transducer as probe 214 in FIG. 2. High pressure chamber 1006 may be cylindrical in shape with an inner diameter of 11.2 cm and a height of 7 cm. High pressure chamber 1006 may have walls, a bottom, and upper lid made of aluminum. The walls may be 4.5 cm thick, and the bottom and the lid may be 3.6 cm thick, to sustain high pressures.

In some embodiments, absorber 1008 may be a 1 cm thick acoustic rubber placed on the bottom of high pressure chamber 1006 to dampen possible reverberations during stone imaging. Stone 1010 may be immersed in water 1012 and fixed on the tip of a brass needle 1.6 mm in diameter that is attached to a wall of high pressure chamber 1006 by stone holder 1016. Acoustic window 1014 may be a polystyrene puck fixed in the middle of the lid to serve as an acoustic window for better ultrasound transmission.

In some embodiments, on top of the lid of high pressure chamber 1004, a plastic cylinder of 8.8 cm diameter and 5.1 cm height may be attached to form an external water tank, where transducer 1002 may immersed. Transducer 1002 may be fixed on the positioning system with its axis oriented perpendicularly to the lid of high pressure chamber 1004. The surface of the transducer 1002 may be close (less than 1 mm) but may not touch acoustic window 1014 during experimentation. As such, transducer displacement caused by acoustic window 1014 bending under high-pressure may be prevented. The transversal position of transducer 1002 may be adjusted by the positioning system to find the optimal location on the stone for detecting the excited characteristics.

In some embodiments, high static pressure may be generated inside high pressure chamber 1004 by a piston screw pump (not shown in FIG. 10). This pump may be capable of producing pressure up to 200 MPa. However, lower pressures (less than 9 MPa) may be used since higher pressures may exceed several times the peak negative pressure of the ultrasound pulses. A gauge of maximum scale of 13.8 MPa may be used for determining pressure in high pressure chamber 1005.

In some embodiments, Doppler imaging may illustrate that pressure in high pressure chamber 1006 may suppress the twinkling or excitation of stone 1010. Compared to ambient pressures, the high pressure applied may suppress the twinkling or excitation of stone 1010 almost completely. Further, by releasing the pressure, the twinkling or excitation of stone 1010 may reappear immediately.

In some embodiments, a pressure threshold may be determined for detecting an excited object. For example, the pressure of high pressure chamber 1006 may be monitored such that if the pressure exceeds the pressure threshold for detecting stone 1010, an indication may be provided. In some instances, a pressure threshold may vary from 0.34 MPa to 1.38 MPa under conditions shown in FIG. 10. Further, in some instances the pressure threshold may be 0.34 MPa to 1.72 MPa. As such, the pressure threshold may vary according to different stones and/or different conditions.

In some embodiments, monitoring the pressure of a medium encompassing a stone may determine the positive and negative pressures for a transducer. For example, under a given pressure, positive pressures (P+) and negative pressures (P−) of pressure detections signals may be 2 MPa and −1 MPa, respectively, to induce an excited state of an object. As such, it should be noted that the pressure of a medium encompassing the stone may be monitored and used to produce detection signals to induce the excited state of stone 1010.

5. ADDITIONAL IMPLEMENTATIONS, APPLICATIONS, AND EXAMPLES

The examples discussed hereafter are for purposes of illustrating how the subject matter of the present application may be implemented for different applications, such as for medical and/or diagnostic applications. In particular, the examples discussed hereafter provide illustrations regarding possibly ways to implement and utilize features described in this application. The following examples are not meant to be limiting or restrictive of the scope of the present application.

Real human kidney stones were either embedded in a degassed gel block, or in degassed water. The human kidney stones consisted of more than 90% calcium oxalate monohydrate and were 5-12 mm in diameter with submicron bubbles trapped in crevices on the stone surface. The kidney stones were placed in gel and in water. The gel used was polyacrylamide hydrogel, which mimicked tissue structure. The liquid mixture was first degassed for at least one hour in a desiccant chamber before commencing experimentations.

An ultrasound engine was used to determine the presence of the kidney stone. The ultrasound engine achieved the results below by utilizing a 128 element linear ultrasound array with a 5 MHz central frequency with a clinical probe. The reflection signals were received by a broadband calibrated hydrophone with a sensitivity of 48 nV/Pa at 5 MHz. The acoustic pulse was similar to the transducer voltage with a form of a 3-cycle tone burst with a central frequency of 5 MHz.

The kidney stones were positioned 4 cm from the ultrasound probe and were immersed within the tissue-mimicking gel. At the location 4 cm away from the transducer in water, the measured peak positive and negative pressures were 2 MPa and −1 MPa, respectively. These values aided choosing sufficiently high levels of the static pressure in an overpressure test. The imaging was performed in a "flash" transmitting mode when all the array elements were excited simultaneously to emit a quasi-plane wave in the direction orthogonal to the radiating surface (zero degrees incident angle). Such a mode simplified the analysis of the reflection signals without limiting the possibility of stone imaging. Both B-mode and Doppler mode were employed. In the Doppler mode, the array elements were excited by a series of 14 identical pulses emitted one-after-another with 3 kHz pulse-repetition frequency (PRF). The PRF was adjustable. Each pulse in the 14 pulse was a tone burst consisting of three cycles at the central frequency 5 MHz.

The reflection signals were received when the detection signals reflected from the kidney stone and returned to the probe. The corresponding reflection signals of the array elements went through an anti-aliasing band-pass filter of 0.7-17 MHz bandwidth, an amplifier with the time-gain compensating (TGC) feature, a clipping diode (to limit excessive signals), and were sampled at a 20 MHz frequency by a 12-bit analog-to-digital convertor (ADC). The digitized signals were processed in real-time using in-house code written in a mathematical software platform. The signals were also stored in a buffer and were able to be post-processed at a later time. The saved signals were radio-frequency (RF) data output from the ADC's for each channel. Access to this RF data provided a possibility to study the "raw" ultrasound signals associated with the excited kidney stone.

FIG. 7A shows typical signals that were analyzed to reveal the features of the excited kidney stone. FIGS. 7A and 7B, describe data for imaging the natural kidney stones, which were placed in the gel. As noted, FIG. 7A overlays 12 successive reflection signals 701-712 of the Doppler ultrasound pulses reflected from the stone and recorded at the central element of the array. The imaging depth d corresponded to the time delay of the reflected signal t in accordance with the formula $d=c*t/2$, where $c=1540$ m/s. The signals 701-712 that were plotted on top of each other are barely distinguishable, because the corresponding changes are small.

To easier reveal the difference between reflection signals 701-712, the Doppler power was calculated from those waveforms. The Doppler power is shown in FIG. 7B. The Doppler power was provided on a dB scale, relative to the background noise level. The essential spike occurred about 2-3 microseconds after the arrival of the front of the reflection signals 701-712, which indicated that the corresponding part of the signal within the Doppler signal was fluctuating from pulse to pulse. Such a spike was observed for all studied stones and corresponded to exciting the kidney stone of the color Doppler image. This illustrated detecting the excited kidney stones.

FIG. 7C shows signals obtained for a simulated acoustic source test. The simulated Doppler signals shown in FIG. 7C provide 12 signals that were plotted on top of each other. The signals in FIGS. 7C and 7D were visually identical, which indicated a high quality of the mimicking procedure. The artificial Doppler signals 721-732 were sent through the same signal path inside the machine as the signals 701-712.

FIG. 7D represents the result for the Doppler power calculated from the signals 721-732. No obvious spike was seen, as shown in FIG. 7D. This test was repeated for six kidney stones, and the result was repeatable. This observation provided the conclusion that the origin for determining the presence of an excited kidney stone is not related to a machine or signal processing. Therefore, detecting the excited kidney stone resulted from an acoustic effect.

The results indicated that the kidney stones were detected from bubbles on the kidney stones. The gas bubbles interacted stochastically with ultrasound. The bubbles were either present in the bulk of propagation medium, or they may were resting on the stone surface, especially if there were microscopic crevices. From the pressure tests, there was a strong indication that the reflection signals determined the excited kidney stones from gas bubbles, presumably shrunken but stabilized in crevices on the stone surface. These bubbles shrunk with an increase in pressure but returned when the pressure is released.

From these experiments, the conclusion is that 1) the detection signals excited the kidney stone and analyzing the reflection signals determined the kidney stone in the excited state, 2) detecting an excited kidney stone was related to acoustic effects and not by abnormal responses of a machine's electronic circuitry or improper signal processing; and 3) detection was suppressed by overpressure and by better wetting of the stone surface. These results further conclude that detecting the kidney stone in the excited state was caused by small bubbles that sit on the irregularities or in crevices on the stone surface.

6. CONCLUSION

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying Figures. In the Figures, similar symbols typically identify similar components, unless context dictates otherwise. It will be readily understood that the aspects of the present disclosure, as generally described herein, and illustrated in the Figures, can be arranged, substituted, combined, separated, and designed in a wide variety of different configurations, all of which are explicitly contemplated herein.

With respect to any or all of the diagrams, scenarios, and flow charts in the Figures and as discussed herein, each block and/or communication can represent a processing of information and/or a transmission of information in accordance with example embodiments. Alternative embodiments are included within the scope of these example embodiments. In these alternative embodiments, for example, functions described as blocks, transmissions, communications, requests, responses, and/or messages can be executed out of order from that shown or discussed, including substantially concurrent or in reverse order, depending on the functionality involved. Further, more or fewer blocks and/or functions can be used with any of the ladder diagrams, scenarios, and flow charts discussed herein, and these ladder diagrams, scenarios, and flow charts can be combined with one another, in part or in whole.

A block that represents a processing of information can correspond to circuitry that can be configured to perform the specific logical functions of a herein-described method or technique. Alternatively or additionally, a block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk or hard drive or other storage medium.

The computer readable medium can also include physical and/or non-transitory computer readable media such as computer-readable media that stores data for short periods of time like register memory, processor cache, and random access memory (RAM). The computer readable media can also include physical and/or non-transitory computer readable media that stores program code and/or data for longer periods of time, such as secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

Moreover, a block that represents one or more information transmissions can correspond to information transmissions between software and/or hardware modules in the same physical device. However, other information transmissions can be between software modules and/or hardware modules in different physical devices.

The particular arrangements shown in the Figures should not be viewed as limiting. It should be understood that other embodiments can include more or less of each element shown in a given Figure. Further, some of the illustrated elements can be combined or omitted. Yet further, an example embodiment can include elements that are not illustrated in the Figures.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A method of detecting a concretion object or a calcification object within a living body, comprising:
    inducing an excited state of the object by transmitting one or more first ultrasound pulses into a medium that surrounds the object, wherein the excited state is characterized by varying a size or a shape of a bubble attached to the object, wherein the object in a non-excited state has a first ultrasound reflection characteristics and the object in the excited state has a second ultrasound reflection characteristics, and wherein the first ultrasound reflection characteristics is different from the second ultrasound reflection characteristics;
    transmitting one or more second ultrasound pulses into the medium towards the object in the excited state, wherein the second ultrasound pulses have a lower amplitude than the first ultrasound pulses;
    detecting one or more second ultrasound reflections of the one or more second ultrasound pulses off of the object in the excited state; and
    determining that the object is present in the medium based on detecting the one or more second ultrasound reflections off of the object in the excited state.

2. The method of claim 1, wherein the one or more first ultrasound pulses induce the excited state of the object by causing the bubble attached to the object to increase in size.

3. The method of claim 1, wherein determining that the object is present comprises detecting a Doppler shift in the one or more second ultrasound reflections.

4. The method of claim 1, wherein determining that the object is present comprises detecting a B-mode signal in the one or more second ultrasound reflections.

5. The method of claim 1, wherein at least one of the one or more second ultrasound pulses has a burst of about 5 microseconds.

6. The method of claim 1, wherein the one or more second ultrasound pulses have a pulse repetition period of about 160 microseconds.

7. The method of claim 1, wherein the one or more second ultrasound pulses have a pulse repetition period of about 333 microseconds.

8. The method of claim 1, wherein the one or more second ultrasound pulses include an ultrasound wave having a frequency within a range from 2 MHz to 8 MHz.

9. The method of claim 1, wherein the one or more second ultrasound pulses have a pulse repetition frequency within a range of 1 kHz to 5 kHz.

10. A device for detecting a concretion object or a calcification object within a living body, comprising:
    a processor;
    an ultrasound probe; and
    a non-transitory computer-readable medium storing program instructions that, when executed by the processor, cause the device to perform functions comprising:
        inducing an excited state of the object by transmitting one or more first ultrasound pulses into a medium that surrounds the object, wherein the excited state is characterized by varying a size or a shape of a bubble attached to the object, wherein the object in a non-excited state has a first ultrasound reflection characteristics and the object in the excited state has a second ultrasound reflection characteristics, and wherein the first ultrasound reflection characteristics is different from the second ultrasound reflection characteristics;
        transmitting one or more second ultrasound pulses into the medium towards the object in the excited state, wherein the second ultrasound pulses have a lower amplitude than the first ultrasound pulses;
        detecting one or more second ultrasound reflections of the one or more second ultrasound pulses off of the object in the excited state; and
        determining that the object is present in the medium based on detecting the one or more second ultrasound reflections off of the object in the excited state.

11. The device of claim 10, wherein the one or more first ultrasound pulses induce the excited state of the object by causing the bubble attached to the object to oscillate.

12. The device of claim 10, wherein the one or more second ultrasound pulses include an ultrasound wave having a frequency within a range from 2 MHz to 8 MHz.

13. The device of claim 10, wherein the one or more second ultrasound pulses have a pulse repetition frequency within a range of 1 kHz to 5 kHz.

14. A non-transitory computer-readable medium storing program instructions that, when executed by a device, cause the device to detect a concretion object or a calcification object within a living body by performing functions comprising:

inducing an excited state of the object by transmitting one or more first ultrasound pulses into a medium that surrounds the object, wherein the excited state is characterized by varying a size or a shape of a bubble attached to the object, wherein the object in a non-excited state has a first ultrasound reflection characteristics and the object in the excited state has a second ultrasound reflection characteristics, and wherein the first ultrasound reflection characteristics is different from the second ultrasound reflection characteristics;

transmitting one or more second ultrasound pulses into the medium towards the object in the excited state, wherein the second ultrasound pulses have a lower amplitude than the first ultrasound pulses;

detecting one or more second ultrasound reflections of the one or more second ultrasound pulses off of the object in the excited state; and determining that the object is present in the medium based on detecting the one or more second ultrasound reflections off of the object in the excited state.

15. The non-transitory computer-readable medium of claim 14, wherein the one or more first ultrasound pulses induce the excited state of the object by causing the bubble attached to the object to increase in size.

16. The non-transitory computer-readable medium of claim 14, wherein the one or more first ultrasound pulses induce the excited state of the object by causing the bubble attached to the object to oscillate.

17. The non-transitory computer-readable medium of claim 14, wherein determining that the object is present comprises detecting a Doppler shift in the second ultrasound reflections.

18. The non-transitory computer-readable medium of claim 14, wherein determining that the object is present comprises detecting a B-mode signal in the second ultrasound reflections.

19. The non-transitory computer-readable medium of claim 14, wherein determining that the object is present comprises detecting phase variations or phase variability in the second ultrasound reflections.

20. The non-transitory computer-readable medium of claim 14, wherein a duration of transmitting one or more first ultrasound pulses toward the object is 200-400 microseconds.

\* \* \* \* \*